United States Patent
Hays et al.

(10) Patent No.: US 8,168,802 B2
(45) Date of Patent: May 1, 2012

(54) RING CLOSING AND RELATED METHODS AND INTERMEDIATES

(75) Inventors: David S. Hays, Woodbury, MN (US); Sonja S. Mackey, St. Paul, MN (US); William H. Moser, St. Paul, MN (US); Doris D. Stoermer, White Bear Lake, MN (US); Matthew R. Radmer, North Robbinsdale, MN (US); Shri Niwas, Maple Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 877 days.

(21) Appl. No.: 11/887,525

(22) PCT Filed: Mar. 31, 2006

(86) PCT No.: PCT/US2006/012022
§ 371 (c)(1),
(2), (4) Date: Oct. 6, 2008

(87) PCT Pub. No.: WO2006/121528
PCT Pub. Date: Nov. 16, 2006

(65) Prior Publication Data
US 2011/0269965 A1    Nov. 3, 2011

Related U.S. Application Data

(60) Provisional application No. 60/667,840, filed on Apr. 1, 2005.

(51) Int. Cl.
*C07D 233/70* (2006.01)
*C07D 233/66* (2006.01)
*C07D 471/00* (2006.01)

(52) U.S. Cl. .................. 548/326.5; 548/337.1; 546/82

(58) Field of Classification Search ............... 548/326.5, 548/337.1; 546/82
See application file for complete search history.

(56) References Cited

U.S. PATENT DOCUMENTS

| | | | |
|---|---|---|---|
| 3,450,693 A | 6/1969 | Katsumi et al. | |
| 4,420,617 A | 12/1983 | Lesher et al. | |
| 6,677,349 B1 | 1/2004 | Griesgraber | |
| 7,879,849 B2 * | 2/2011 | Hays et al. | 514/232.8 |
| 2004/0204436 A1 | 10/2004 | Gerster et al. | |

FOREIGN PATENT DOCUMENTS

| | | |
|---|---|---|
| EP | 0 645 389 A1 | 3/1995 |
| EP | 1 256 582 A1 | 11/2002 |
| EP | 1256582 * | 11/2002 |
| WO | 01/46190 | 6/2001 |
| WO | WO 01/46190 * | 6/2001 |

OTHER PUBLICATIONS

Extended European Search Report for 06769789.6 mailed Apr. 8, 2010.
Hoffman et al., Conformational requirements for histamine H2-receptor inhibitors: a structure-activity study of phenylene analogues related to cimetidine and tiotidine. J Med Chem. Feb. 1983;26(2):140-4.
Minakawa, N. et al, New Base Pairing Motifs. The synthesis and Thermal Stability of Oligodeoxynucleotides Containing Imidazopyridopyrimidine Nucleosides with the Ability to Form Four Hydrogen Bonds, Journal of the American Chemical Society, 2003, vol. 125, No. 33, pp. 9970-9982.

* cited by examiner

*Primary Examiner* — Nizal Chandrakumar

(57) ABSTRACT

Methods and intermediates useful for making compounds of the formula: and the preparation of compounds of Formula I, preferably including the formation of intermediate compounds of the formula:

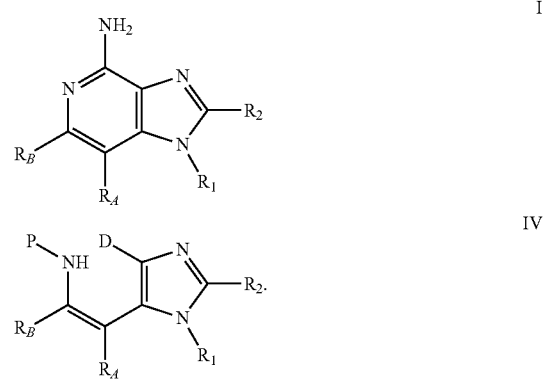

21 Claims, No Drawings

RING CLOSING AND RELATED METHODS AND INTERMEDIATES

RELATED APPLICATION

This application is a national stage filing under 35 U.S.C. §371 of PCT International application PCT/US2006/012022 designating the United States of America, and filed Mar. 31, 2006. This application claims the benefit under 35 U.S.C. §119(e) of U.S. provisional application Ser. No. 60/667,840, filed Apr. 1, 2005, which is incorporated herein by reference.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other mechanisms. Thus, there is a need for methods and intermediates for making such compounds.

SUMMARY

The present invention provides various methods and intermediates that are useful for making compounds that can be used to induce cytokine biosynthesis in animals. Such compounds are of the formula:

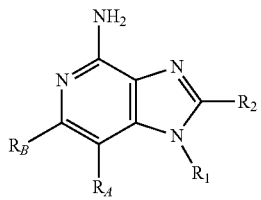

I wherein $R_1$, $R_2$, $R_A$, and $R_B$ are defined hereinbelow. The preparation of compounds of Formula I preferably includes the formation of intermediate compounds of the formula:

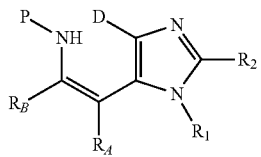

IV wherein $R_1$, $R_2$, $R_A$, $R_B$, P, and D are defined hereinbelow.

In one embodiment, there is provided a method that includes combining a compound of the formula:

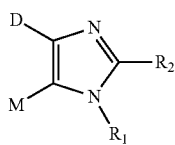

IIIa with a compound of the formula:

IIa or a salt thereof to form a compound of Formula I. In another embodiment, there is provided a method that includes combining a compound of Formula IIIa with a compound of Formula IIa or a salt thereof to form a compound of Formula IV. In certain embodiments, compounds of Formula IV are formed prior to forming compounds of Formula I. In certain embodiments, the intermediate compounds of Formula IV can be isolated if desired.

In one embodiment, there is provided a method that includes combining a compound of the formula:

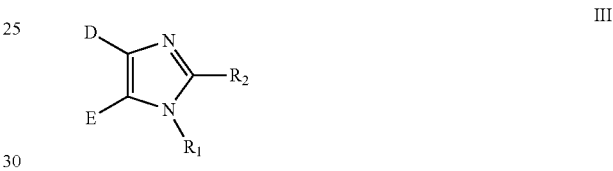

III with a compound of the formula:

II or a salt thereof to form a compound of Formula I. In another embodiment, there is provided a method that includes combining a compound of Formula III with a compound of Formula II or a salt thereof to form a compound of Formula IV. In certain embodiments, compounds of Formula IV are formed prior to forming compounds of Formula I. In certain embodiments, the intermediate compounds of Formula IV can be isolated if desired.

In the compounds of Formulas II, IIa, III, and IIIa, D is selected from the group consisting of —C≡N, —C(O)—O—$C_{1-4}$alkyl, —C(O)—$NH_2$, —C(O)—H, —$CH_2OH$, and —$CH_2OC_{1-4}$alkyl (for certain embodiments, D is preferably —C≡N); E is selected from the group consisting of —Cl, —Br, —I, —OS(O)$_2CF_3$, and —$N_2^+BF_4^-$ (for certain embodiments, E is selected from the group consisting of —Cl, —Br, —I, and —OS(O)$_2CF_3$); M is selected from the group consisting of —B(OH)$_2$, —B(O-alkyl)$_2$, —Sn(alkyl)$_3$, —Zn-Halide,

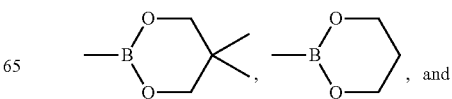, and

-continued

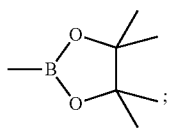

P is selected from the group consisting of hydrogen, —C(O)—C$_{1-4}$alkyl, —C(O)—O—C$_{1-4}$alkyl, benzyl, and p-methoxybenzyl, or —NHP is replaced by a 2,5-dimethylpyrrole (for certain embodiments, P is preferably hydrogen); and R$_1$, R$_2$, R$_A$, and R$_B$ are defined hereinbelow.

In certain embodiments, compounds of Formula III can be prepared from compounds of the formula:

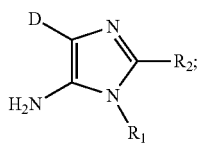

X wherein D is selected from the group consisting of —C≡N, —C(O)—O—C$_{1-4}$alkyl, —C(O)—NH$_2$, —C(O)—H, —CH$_2$OH, and —CH$_2$OC$_{1-4}$alkyl (for certain embodiments, D is preferably —C≡N), and R$_1$ and R$_2$ are defined hereinbelow.

In certain embodiments, compounds of Formula X can be prepared from compounds of the formula:

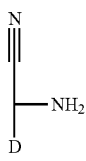

XI in combination with R$_2$C(O-alkyl)$_3$ or R$_2$C(NH)(O-alkyl) in the presence of H$_2$N—R$_1$; wherein D is selected from the group consisting of —C≡N, —C(O)—O—C$_{1-4}$alkyl, —C(O)—NH$_2$, —C(O)—H, —CH$_2$OH, and —CH$_2$OC$_{1-4}$alkyl (for certain embodiments, D is preferably —C≡N), and R$_1$ and R$_2$ are defined hereinbelow.

The present invention also provides a method that includes: providing a compound of the formula:

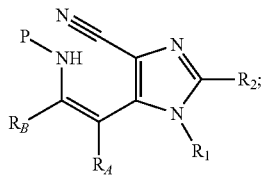

IV' and exposing the compound of Formula IV' to conditions to cause an intramolecular cyclization and formation of a compound of the formula:

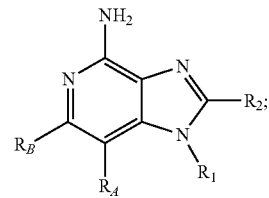

I wherein: P is selected from the group consisting of hydrogen, —C(O)—C$_{1-4}$alkyl, —C(O)—O—C$_{1-4}$alkyl, benzyl, and p-methoxybenzyl, or —NHP is replaced by a 2,5-dimethylpyrrole; and R$_1$, R$_2$, R$_A$, and R$_B$ are defined hereinbelow.

In one embodiment, there is provided a method that includes: providing a mixture that includes isoamyl nitrite and a halogen source; combining the mixture and a compound of the formula:

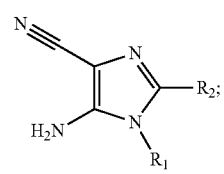

X' and heating the mixture that includes the compound of Formula X' to provide a compound of the formula:

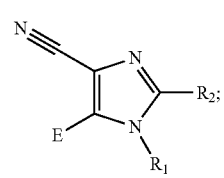

III' wherein E is selected from the group consisting of —Cl, —Br, and —I and R$_1$ and R$_2$ are as defined hereinbelow.

In one embodiment, there is provided a method that includes: providing a salt of a compound of the formula:

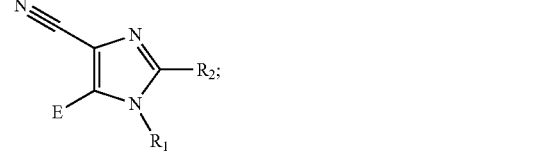

XI combining the salt of the compound of Formula XI with a tertiary amine to form the free base of the compound of Formula XI; and combining the free base of the compound of Formula XI with R$_2$C(O-alkyl)$_3$ or R$_2$C(NH)(O-alkyl) in the presence of H$_2$N—R$_1$ to form a compound of the formula:

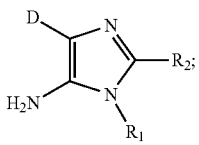

wherein D is selected from the group consisting of —C≡N and $R_1$ and $R_2$ are defined hereinbelow.

In one embodiment, there is provided a method that includes: providing a salt of a compound of the formula:

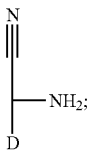

combining the salt of the compound of Formula XI with pyridine to form the free base of the compound of Formula XI; and combining the free base of the compound of Formula XI with $R_2C(O\text{-alkyl})_3$ or $R_2C(NH)(O\text{-alkyl})$ in the presence of $H_2N$—$R_1$ to form a compound of the formula:

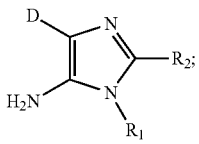

wherein D is selected from the group consisting of —C≡N and $R_1$ and $R_2$ are defined hereinbelow. These methods can further include: providing a mixture comprising isoamyl nitrite and a halogen source; combining the mixture and the compound of the formula:

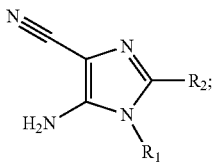

heating the mixture comprising the compound of Formula X' to provide a compound of the formula:

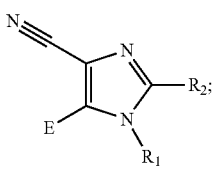

wherein E is selected from the group consisting of —Cl, —Br, and —I.

In one embodiment, there is provided an intermediate compound of the formula

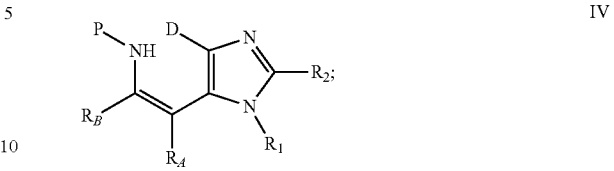

wherein $R_1$, $R_2$, $R_A$, $R_B$, P, and D are defined hereinbelow.

The compounds of Formula I are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

As used herein, "a", "an", "the", "at least one", and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides various methods and intermediates useful for making compounds of the formula:

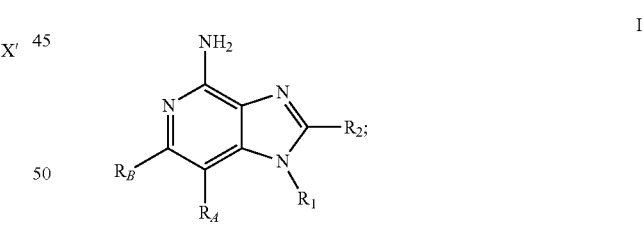

wherein $R_1$, $R_2$, $R_A$, and $R_B$ are defined hereinbelow. The preparation of compounds of Formula I preferably includes the formation of intermediate compounds of the formula:

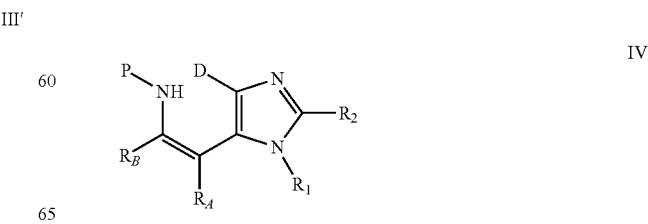

wherein $R_1$, $R_2$, $R_A$, $R_B$, P, and D are defined hereinbelow.

In one embodiment, the present invention provides a method (i) that includes:
combining a compound of the formula:

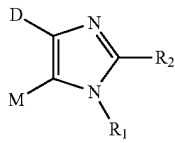
IIIa with a compound of the formula:

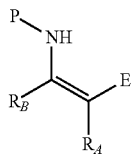
IIa or a salt thereof
or
combining a compound of the formula:

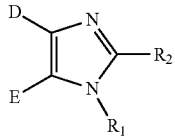
III with a compound of the formula:

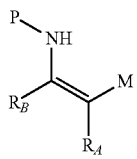
II or a salt thereof to form a compound of the formula:

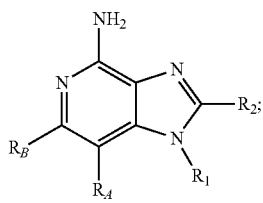
I wherein:
D is selected from the group consisting of —C≡N, —C(O)—O—$C_{1-4}$alkyl, —C(O)—$NH_2$, —C(O)—H, —$CH_2OH$, and —$CH_2OC_{1-4}$alkyl;
E is selected from the group consisting of —Cl, —Br, —I, —$OS(O)_2CF_3$, and —$N_2^+BF_4^-$;
M is selected from the group consisting of —$B(OH)_2$, —$B(O\text{-alkyl})_2$, —$Sn(\text{alkyl})_3$, —Zn-Halide,

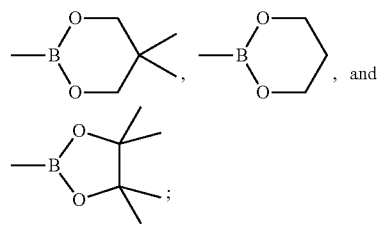
, and

P is selected from the group consisting of hydrogen, —C(O)—$C_{1-4}$alkyl, —C(O)—O—$C_{1-4}$alkyl, benzyl, and p-methoxybenzyl, or —NHP is replaced by a 2,5-dimethylpyrrole;
$R_A$ and $R_B$ taken together form a fused benzene ring or fused pyridine ring wherein the benzene ring or pyridine ring is unsubstituted or substituted by one or more groups that do not interfere with the immunomodulating activity of the compound of Formula I;
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
—O—,
—$S(O)_{0-2}$—,
—$S(O)_2$—$N(R_8)$—,
—$C(R_6)$—,
—$C(R_6)$—O—,
—O—$C(R_6)$—,
—O—C(O)—O—,
—$N(R_8)$-Q-,
—$C(R_6)$—$N(R_8)$—,
—O—$C(R_6)$—$N(R_8)$—,
—$C(R_6)$—$N(OR_9)$—,
—O—$N(R_8)$-Q-,
—O—N=$C(R_4)$—,
—C(=N—O—$R_8$)—,
—CH(—N(—O—$R_8$)-Q-$R_4$)—,

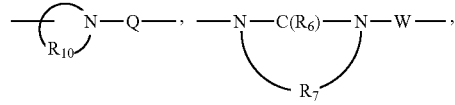

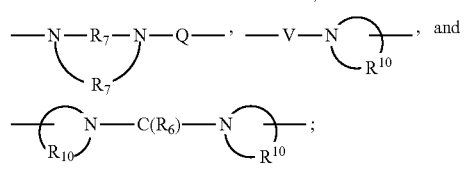

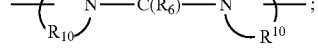

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of:

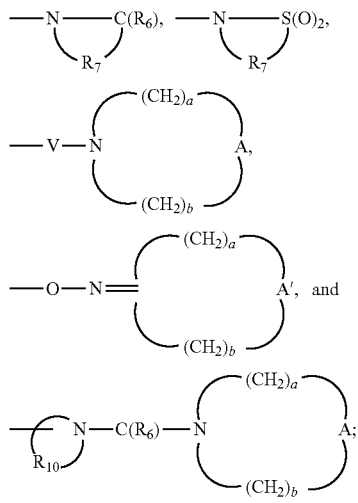

R₆ is selected from the group consisting of =O and =S;
R₇ is C₂₋₇ allylene;
R₈ is selected from the group consisting of hydrogen, alkyl, alkoxyalkylenyl, hydroxyalkylenyl, arylalkylenyl, and heteroarylalkylenyl;
R₉ is selected from the group consisting of hydrogen and alkyl;
R₁₀ is C₃₋₈ alkylene;
A is selected from the group consisting of —O—, —C(O)—, —S(O)₀₋₂—, and —N(R₄)—;
A' is selected from the group consisting of —O—, —S(O)₀₋₂—, —N(-Q-R₄)—, and —CH₂—;
Q is selected from the group consisting of a bond, —C(R₆)—, —C(R₆)—C(R₆)—, —S(O)₂—, —C(R₆)—N(R₈)—W—, —S(O)₂—N(R₈)—, —C(R₆)—O—, —C(R₆)—S—, and —C(R₆)—N(OR₉)—;
V is selected from the group consisting of —C(R₆)—, —O—C(R₆)—, —N(R₈)—C(R₆)—, and —S(O)₂—;
W is selected from the group consisting of a bond, —C(O)—, and —S(O)₂—; and
a and b are independently integers from 1 to 6 with the proviso that a+b is ≦7.

In certain embodiments of such methods, R_A and R_B taken together form a fused benzene ring or fused pyridine ring wherein the benzene ring or pyridine ring is unsubstituted or substituted by one or more R groups, or substituted by one R₃ group, or substituted by one R₃ group and one R group; wherein:

R is selected from the group consisting of:
halogen,
hydroxy,
alkyl,
haloalkyl,
alkoxy, and
N(R₉)₂;

R₃ is selected from the group consisting of:
—Z—X—R₄,
—Z—X—R₄,
—Z—X—Y—R₄,
—Z—X—Y—X—Y—R₄, and
—Z—X—R₅; and Z is a bond or —O—.

In certain embodiments of such methods, E is selected from the group consisting of —Cl, —Br, —I, and —OS(O)₂CF₃.

In certain embodiments of such methods, heating occurs before, during, or after combining the compounds.

In certain embodiments of such methods, combining the compounds occurs in the presence of a palladium catalyst when M is selected from the group consisting of —B(OH)₂, —B(O-alkyl)₂,

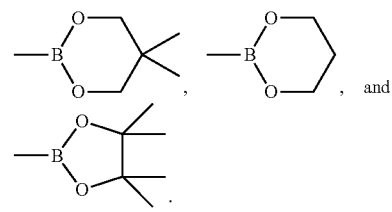

In certain embodiments of such methods, combining the compounds occurs in the presence of a palladium catalyst and a base when M is selected from the group consisting of —B(OH)₂, —B(O-alkyl)₂,

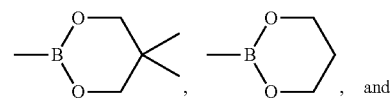

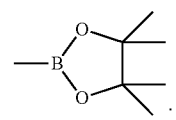

In certain embodiments of such methods, combining the compounds occurs in the presence of a palladium catalyst when M is —Sn(alkyl)₃.

In certain embodiments of such methods, combining the compounds occurs in the presence of a nickel or palladium catalyst when M is —Zn-Halide.

In certain embodiments of such methods, combining the compounds of Formulas II and III or IIa and IIIa forms an intermediate of the formula:

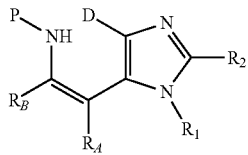

IV prior to forming a compound of Formula I. In certain embodiments of such methods, the intermediate of Formula IV is isolated. In certain embodiments of such methods, D is —C≡N.

In certain embodiments of such methods, D is —C(O)—H or —C(O)—O—$C_{1-4}$alkyl and P is hydrogen.

In certain embodiments of such methods, when D is —C(O)—H combining the compounds forms an intermediate of the formula:

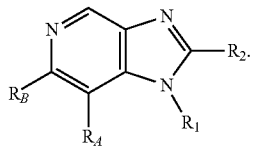

XX

In certain embodiments of such methods, the compound of Formula XX is oxidized to a form a 5N-oxide. In certain embodiments of such methods, the 5N-oxide is converted to an ester and then the ester is reacted with an aminating agent to form a compound of the formula:

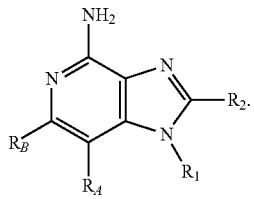

I

In certain embodiments of such methods, when D is —C(O)—O—$C_{1-4}$alkyl combining the compounds forms an intermediate of the formula:

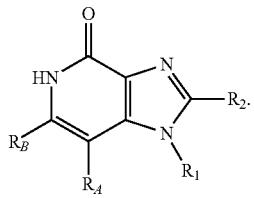

XVII

In certain embodiments of such methods, the compound of Formula XVII is chlorinated to form a compound of the formula:

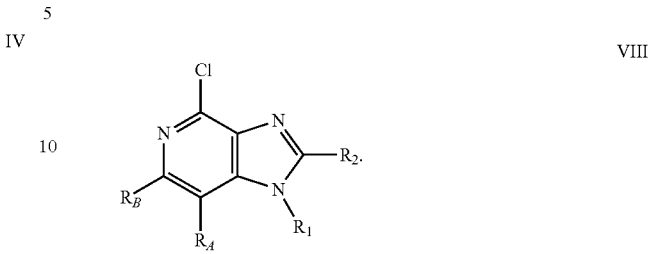

VIII

In certain embodiments of such methods, the compound of Formula VIII is aminated to form a compound of the formula:

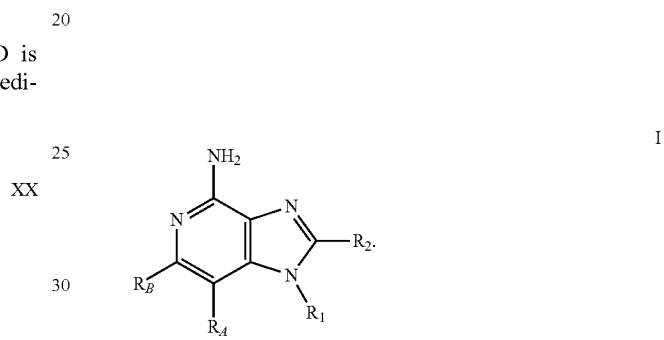

I

In certain embodiments, such methods further include: providing a compound of the formula:

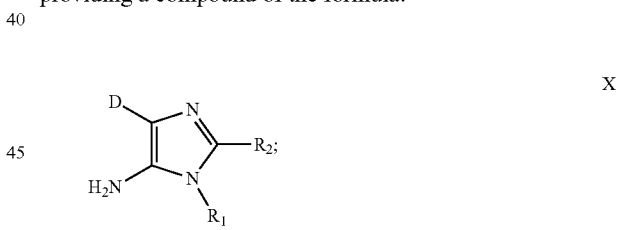

X and converting the compound of Formula X to a compound of Formula III prior to combining the compounds of Formulas III and II. In certain of these embodiments, such methods include providing a mixture comprising isoamyl nitrite and a halogen source; combining the mixture and a compound of the formula:

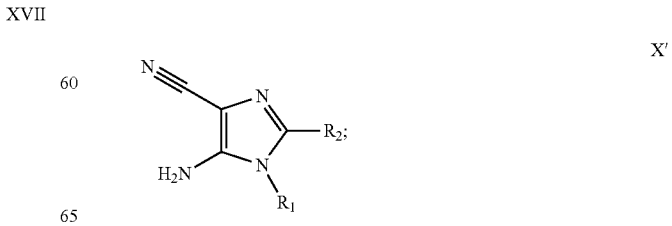

X' and heating the mixture comprising the compound of Formula X' to provide a compound of the formula:

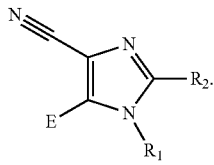

III'

In certain embodiments, such methods further include: providing a compound of the formula:

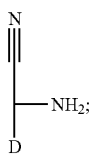

XI and combining the compound of Formula XI with $R_2C(O\text{-alkyl})_3$ or $R_2C(NH)(O\text{-alkyl})$ in the presence of $H_2N\text{—}R_1$ to form a compound of Formula X. In certain of these embodiments, such methods comprise providing a salt of a compound of the formula XI; combining the salt of the compound of Formula XI with a tertiary amine to form the free base of the compound of Formula XI; and combining the free base of the compound of Formula XI with $R_2C(O\text{-alkyl})_3$ or $R_2C(NH)(O\text{-alkyl})$ in the presence of $H_2N\text{—}R_1$ to form a compound of the formula X. In certain other of these embodiments, such methods comprise providing a salt of a compound of the formula XI; combining the salt of the compound of Formula XI with pyridine to form the free base of the compound of Formula XI; and combining the free base of the compound of Formula XI with $R_2C(O\text{-alkyl})_3$ or $R_2C(NH)(O\text{-alkyl})$ in the presence of $H_2N\text{—}R_1$ to form a compound of the formula X. In certain embodiments of such methods, $R_2C(O\text{-alkyl})_3$ is selected from the group consisting of trimethyl orthoacetate, trimethyl orthobutyrate, trimethyl orthoformate, trimethyl orthovalerate, triethyl orthoacetate, triethyl orthoformate, and triethyl orthopropionate. In certain of these embodiments, $R_2C(O\text{-alkyl})_3$ is triethyl orthoformate or trimethyl orthoformate. In certain other of these embodiments, $R_2C(O\text{-alkyl})_3$ is triethyl orthopropionate. In certain embodiments of such methods, $H_2N\text{—}R_1$ is isobutylamine. In certain other embodiments, $H_2N\text{—}R_1$ is N-(4-aminobutyl) methanesulfonamide hydrochloride.

In certain embodiments of such methods, the compounds of Formulas III and II are combined.

In certain embodiments of such methods, the compounds of Formulas IIIa and IIa are combined.

Conditions of such reactions are described in greater detail hereinbelow.

In one embodiment, the present invention provides a method (ii) that includes:
combining a compound of the formula:

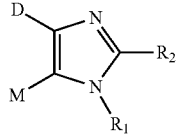

IIIa with a compound of the formula:

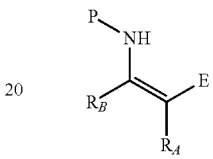

IIa or a salt thereof.
or
combining a compound of the formula:

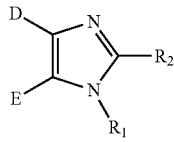

III with a compound of the formula:

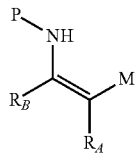

II or a salt thereof to form a compound of the formula:

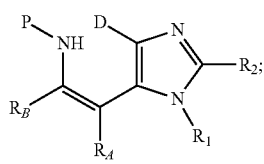

IV wherein:
D is selected from the group consisting of —C≡N, —C(O)—O—$C_{1-4}$alkyl, —C(O)—NH$_2$, —C(O)—H, —CH$_2$OH, and —CH$_2$OC$_{1-4}$alkyl;
E is selected from the group consisting of —Cl, —Br, —I, —OS(O)$_2$CF$_3$, and —N$_2^+$BF$_4^-$;
M is selected from the group consisting of —B(OH)$_2$, —B(O-alkyl)$_2$, —Sn(alkyl)$_3$, —Zn-Halide,

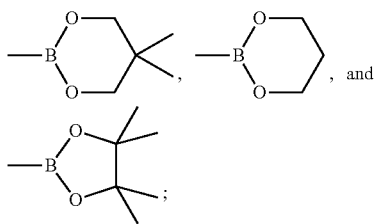, and

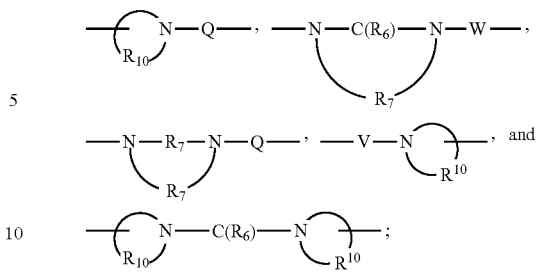

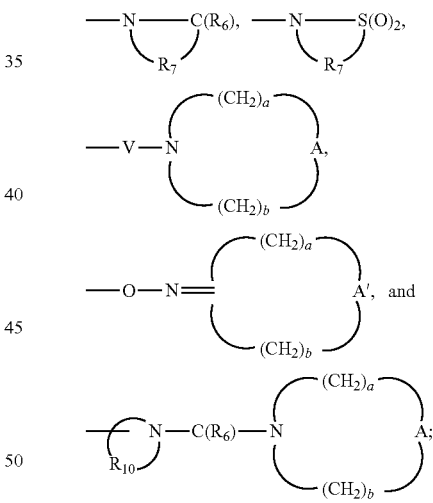

P is selected from the group consisting of hydrogen, —C(O)—$C_{1-4}$alkyl, —C(O)—O—$C_{1-4}$alkyl, benzyl, and p-methoxybenzyl, or —NHP is replaced by a 2,5-dimethylpyrrole;

$R_A$ and $R_B$ taken together form a fused benzene ring or fused pyridine ring wherein the benzene ring or pyridine ring is unsubstituted or substituted by one or more R groups, or substituted by one $R_3$ group, or substituted by one $R_3$ group and one R group; wherein:

R is selected from the group consisting of:
halogen,
hydroxy,
alkyl,
haloalkyl,
alkoxy, and
—N($R_9$)$_2$;

$R_1$ is selected from the group consisting of:
—$R_4$,
—X—$R_4$,
—X—Y—$R_4$,
—X—Y—X—Y—$R_4$, and
—X—$R_5$;

$R_2$ is selected from the group consisting of:
—$R_4$,
—X—$R_4$,
—X—Y—$R_4$, and
—X—$R_5$;

$R_3$ is selected from the group consisting of:
—Z—$R_4$,
—Z—X—$R_4$,
—Z—X—Y—$R_4$,
—Z—X—Y—X—Y—$R_4$, and
—Z—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—, Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, and —N($R_4$)—;
A' is selected from the group consisting of —O—, —S(O)$_{0-2}$—, —N(-Q-$R_4$)—, and —CH$_2$—;
Q is selected from the group consisting of a bond, —C($R_6$)—, —C($R_6$)—C($R_6$)—, —S(O)$_2$—, —C($R_6$)—N (R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7.

In certain embodiments of such methods, E is selected from the group consisting of —Cl, —Br, —I, and —OS(O)$_2$CF$_3$.

In certain embodiments of such methods, heating occurs before, during, or after combining the compounds.

In certain embodiments of such methods, combining the compounds occurs in the presence of a palladium catalyst when M is selected from the group consisting of —B(OH)$_2$, —B(O-alkyl)$_2$,

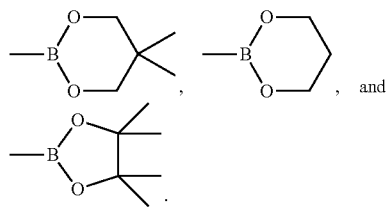

In certain embodiments of such methods, combining the compounds occurs in the presence of a palladium catalyst and a base when M is selected from the group consisting of —B(OH)$_2$, —B(O-alkyl)$_2$,

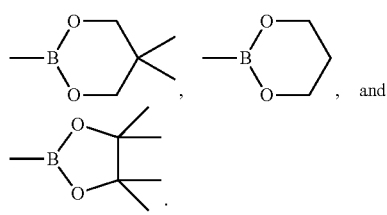

In certain embodiments of such methods, combining the compounds occurs in the presence of a palladium catalyst when M is —Sn(alkyl)$_3$.

In certain embodiments of such methods, combining the compounds occurs in the presence of a nickel or palladium catalyst when M is —Zn-Halide.

In certain embodiments of such methods, D is —C≡N and the compound of Formula IV undergoes an intramolecular cyclization to form a compound of the formula:

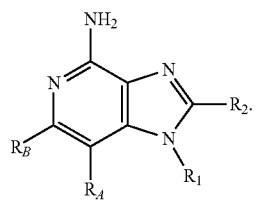

I

In certain embodiments of such methods, P is hydrogen or —C(O)—O—C$_{1-4}$alkyl and the intramolecular cyclization occurs under acidic conditions. In certain embodiments of such methods, P is hydrogen. In certain embodiments of such methods, P is —C(O)—C$_{1-4}$alkyl and the intramolecular cyclization occurs under basic conditions with cleavage of the C$_{1-4}$alkyl group.

In certain embodiments of such methods, D is —C(O)—O—C$_{1-4}$alkyl or —C(O)—NH$_2$ and the compound of Formula IV undergoes an intramolecular cyclization to form a compound of the formula:

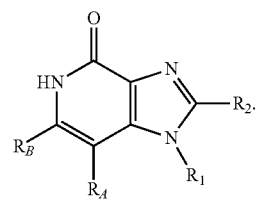

XVII

In certain embodiments of such methods, P is hydrogen or —C(O)—O—C$_{1-4}$alkyl and the intramolecular cyclization occurs under acidic conditions, and the method further comprises chlorinating the compound of Formula XVII to form a compound of the formula:

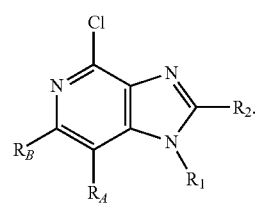

VIII

In certain embodiments of such methods, P is —C(O)—O—C$_{1-4}$alkyl. In certain embodiments of such methods, P is —C(O)—C$_{1-4}$alkyl and the intramolecular cyclization occurs under basic conditions with cleavage of the C$_{1-4}$alkyl group, and the method further comprises chlorinating the compound of Formula XVII to form a compound of the formula:

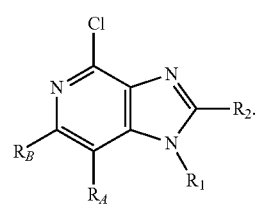

VIII

In certain embodiments, such methods further include aminating the compound of Formula VIII to form a compound of the formula:

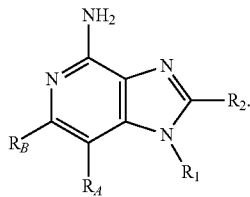

I

In certain embodiments of such methods, D is —C(O)—H, and the compound of Formula IV undergoes an intramolecular cyclization to form a compound of the formula:

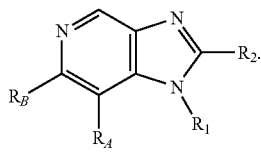

XX

In certain embodiments of such methods, P is hydrogen or —C(O)—O—$C_{1-4}$alkyl and the intramolecular cyclization occurs under acidic conditions, and the method further comprises oxidizing the compound of Formula XX to a form a 5N-oxide. In certain preferred embodiments of such methods, P is —C(O)—O—$C_{1-4}$alkyl. In certain embodiments of such methods, P is —C(O)—$C_{1-4}$alkyl and the intramolecular cyclization occurs under basic conditions with cleavage of the $C_{1-4}$alkyl group, and the method further comprises oxidizing the compound of Formula XX to a form a 5N-oxide. In certain embodiments, such methods further include converting the 5N-oxide to an ester and then reacting the ester with an aminating agent to form a compound of the formula:

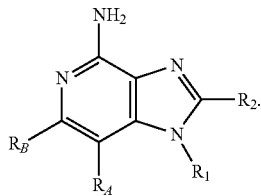

I

In certain embodiments, such methods further include combining the 5N-oxide with trichloroacetyl isocyanate to form an amide, and then hydrolyzing the amide under basic conditions to form a compound of the formula:

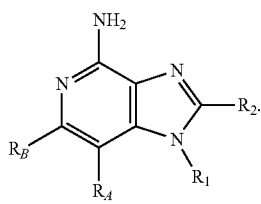

I

In certain embodiments of such methods, D is —C(O)—NH$_2$, and the compound of Formula IV undergoes an intramolecular cyclization in the presence of a dehydrating reagent to form a compound of the formula:

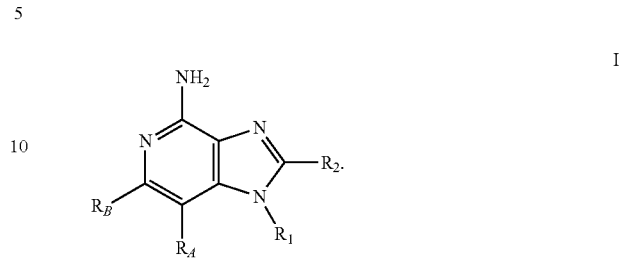

I

In certain embodiments, such methods further include: providing a compound of the formula:

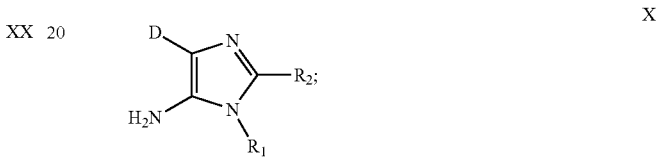

X and converting the compound of Formula X to a compound of Formula III prior to combining the compounds of Formulas III and II. In certain of these embodiments, such methods include providing a mixture comprising isoamyl nitrite and a halogen source; combining the mixture and a compound of the formula:

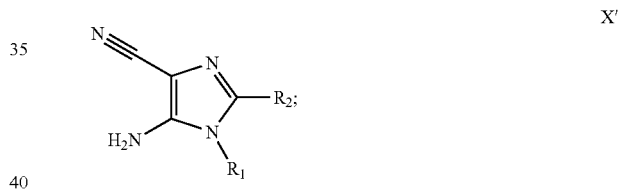

X' and heating the mixture comprising the compound of Formula X' to provide a compound of the formula:

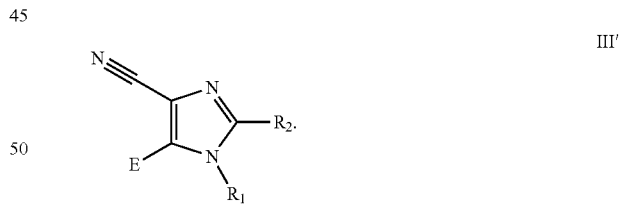

III'

In certain embodiments, such methods further include: providing a compound of the formula:

XI and combining the compound of Formula XI with R$_2$C(O-alkyl)$_3$ or R$_2$C(NH)(O-alkyl) in the presence of H$_2$N—R$_1$ to form a compound of Formula X. In certain of these embodiments, such methods comprise providing a salt of a compound of the formula XI; combining the salt of the compound of Formula XI with a tertiary amine to form the free base of the compound of Formula XI; and combining the free base of the compound of Formula XI with $R_2C(O\text{-alkyl})_3$ or $R_2C(NH)(O\text{-alkyl})$ in the presence of $H_2N\text{—}R_1$ to form a compound of the formula X. In certain other of these embodiments, such methods comprise providing a salt of a compound of the formula XI; combining the salt of the compound of Formula XI with pyridine to form the free base of the compound of Formula XI; and combining the free base of the compound of Formula XI with $R_2C(O\text{-alkyl})_3$ or $R_2C(NH)(O\text{-alkyl})$ in the presence of $H_2N\text{—}R_1$ to form a compound of the formula X. In certain embodiments of such methods, $R_2C(O\text{-alkyl})_3$ is selected from the group consisting of trimethyl orthoacetate, trimethyl orthobutyrate, trimethyl orthoformate, trimethyl orthovalerate, triethyl orthoacetate, triethyl orthoformate, and triethyl orthopropionate. In certain of these embodiments, $R_2C(O\text{-alkyl})_3$ is triethyl orthoformate or trimethyl orthoformate. In certain other of these embodiments, $R_2C(O\text{-alkyl})_3$ is triethyl orthopropionate. In certain embodiments of such methods, $H_2N\text{—}R_1$ is isobutylamine. In certain other embodiments, $H_2N\text{—}R_1$ is N-(4-aminobutyl) methanesulfonamide hydrochloride.

In certain embodiments of such methods, the compounds of Formulas III and II are combined.

In certain embodiments of such methods, the compounds of Formulas IIIa and IIa are combined.

Conditions of such reactions are described in greater detail hereinbelow.

In one embodiment, the present invention provides a method (iii) that includes: providing a compound of the formula:

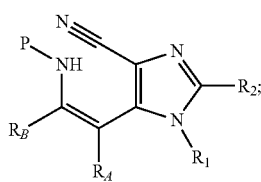

IV' and exposing the compound of Formula IV' to conditions to cause an intramolecular cyclization and formation of a compound of the formula:

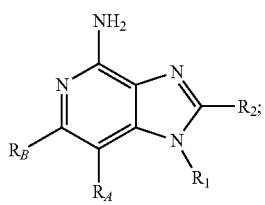

I wherein:
P is selected from the group consisting of hydrogen, —C(O)—$C_{1-4}$alkyl, —C(O)—O—$C_{1-4}$alkyl, benzyl, and p-methoxybenzyl, or —NHP is replaced by a 2,5-dimethylpyrrole;

$R_A$ and $R_B$ taken together form a fused benzene ring or fused pyridine ring wherein the benzene ring or pyridine ring is unsubstituted or substituted by one or more R groups, or substituted by one $R_3$ group, or substituted by one $R_3$ group and one R group; wherein:

R is selected from the group consisting of:
halogen,
hydroxy,
alkyl,
haloalkyl,
alkoxy, and
—N($R_9$)$_2$;

$R_1$ is selected from the group consisting of:
—$R_4$,
—X—$R_4$,
—X—Y—$R_4$,
—X—Y—X—Y—$R_4$, and
—X—$R_5$;

$R_2$ is selected from the group consisting of:
—$R_4$,
—X—$R_4$,
—X—Y—$R_4$, and
—X—$R_5$;

$R_3$ is selected from the group consisting of:
—Z—$R_4$,
—Z—X—$R_4$,
—Z—X—Y—$R_4$,
—Z—X—Y—X—Y—$R_4$, and
—Z—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

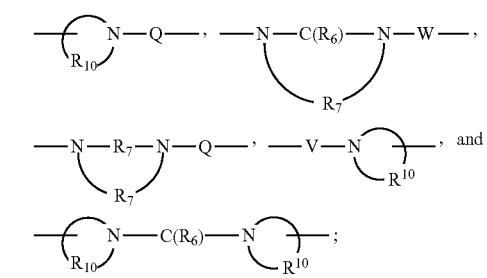

Z is a bond or —O—;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

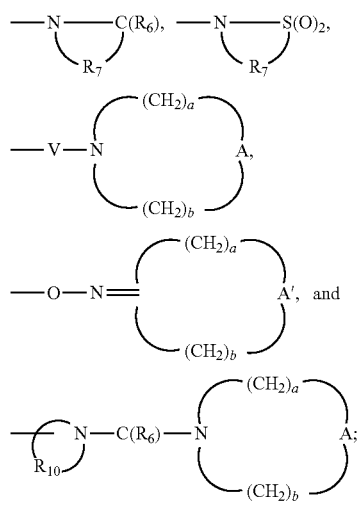

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, and —N(R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7.

In certain embodiments of such methods, P is hydrogen or —C(O)—O—C$_{1-4}$alkyl and the intramolecular cyclization occurs under acidic conditions. In certain embodiments of such methods, P is hydrogen.

In certain embodiments of such methods, P is —C(O)—C$_{1-4}$alkyl and the intramolecular cyclization occurs under basic conditions with cleavage of the C$_{1-4}$alkyl group.

Conditions of such reactions are described in greater detail hereinbelow.

In one embodiment, the present invention provides a method (iv) that includes: providing a mixture comprising isoamyl nitrite and a halogen source; combining the mixture and a compound of the formula:

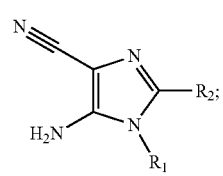

X' and heating the mixture comprising the compound of Formula X' to provide a compound of the formula:

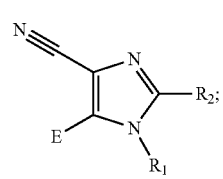

III' wherein:
E is selected from the group consisting of —Cl, —Br, and —I;
$R_1$ is selected from the group consisting of:
—R$_4$,
—X—R$_4$,
—X—Y—R$_4$,
—X—Y—X—Y—R$_4$, and
—X—R$_5$;
$R_2$ is selected from the group consisting of:
—R$_4$,
—X—R$_4$,
—X—Y—R$_4$, and
—X—R$_5$;
X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

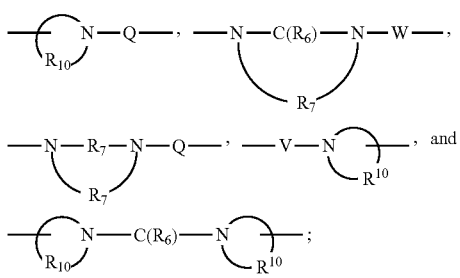

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

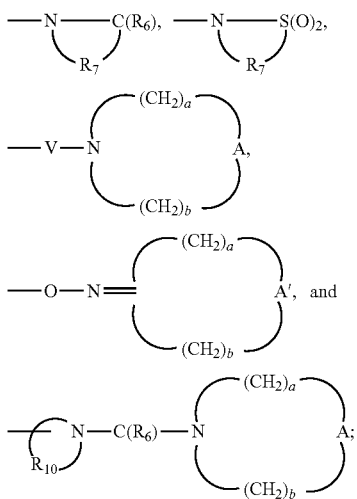

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, and —N(R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7.

In certain embodiments, such methods include the proviso that R$_1$ and R$_2$ do not interfere with the formation of the compound of Formula III'.

In certain embodiments of such methods, the halogen source is iodine. In certain embodiments of such methods, the halogen source is diiodomethane.

In certain embodiments of such methods, heating occurs at a temperature of at least 60° C.

Conditions of such reactions are described in greater detail hereinbelow.

In one embodiment, the present invention provides a method (v) that includes: providing a salt of a compound of the formula:

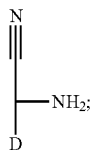

XI combining the salt of the compound of Formula XI with a tertiary amine to form the free base of the compound of Formula XI; and combining the free base of the compound of Formula XI with R$_2$C(O-alkyl)$_3$ or R$_2$C(NH)(O-alkyl) in the presence of H$_2$N—R$_1$ to form a compound of the formula:

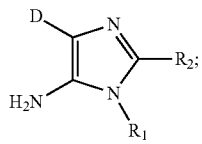

X wherein:
D is selected from the group consisting of —C≡N;
R$_1$ is selected from the group consisting of:
—R$_4$,
—X—R$_4$,
—X—Y—R$_4$,
—X—Y—X—Y—R$_4$, and
—X—R$_5$;
R$_2$ is selected from the group consisting of
—R$_4$,
—X—R$_4$,
—X—Y—R$_4$, and
—X—R$_5$;
X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
—O—,
—S(O)$_{0-2}$—,
—S(O)$_2$—N(R$_8$)—, —C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

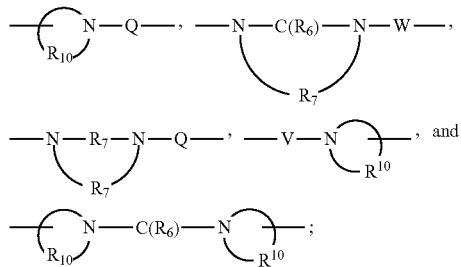

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

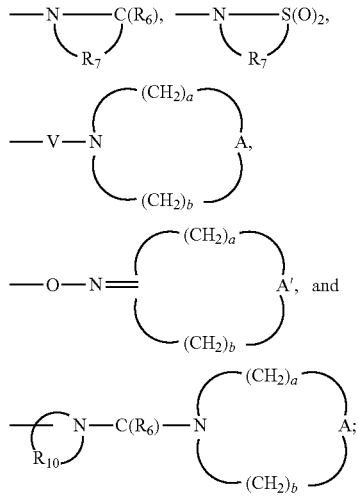

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, and —N($R_4$)—;
A' is selected from the group consisting of —O—, —S(O)$_{0-2}$—, —N(-Q-$R_4$)—, and —CH$_2$—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≦7.

In certain embodiments, such methods include a proviso that $R_1$ and $R_2$ do not interfere with the formation of the compound of Formula X.

In one embodiment, the present invention provides a method (vi) that includes: providing a salt of a compound of the formula:

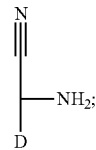

XI combining the salt of the compound of Formula XI with pyridine to form the free base of the compound of Formula XI; and combining the free base of the compound of Formula XI with $R_2C(O-alkyl)_3$ or $R_2C(NH)(O-alkyl)$ in the presence of $H_2N$—$R_1$ to form a compound of the formula:

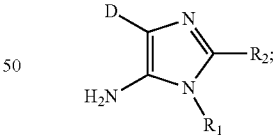

X wherein D, $R_1$, and $R_2$ are as defined above for method (v).

In certain embodiments of such methods, the free base of a compound of Formula XI is combined with $R_2C(O-alkyl)_3$, wherein $R_2C(O-alkyl)_3$ is selected from the group consisting of trimethyl orthoacetate, trimethyl orthobutyrate, trimethyl orthoformate, trimethyl orthovalerate, triethyl orthoacetate, triethyl orthoformate, and triethyl orthopropionate. In certain of these embodiments, $R_2C(O-alkyl)_3$ is triethyl orthoformate or trimethyl orthoformate. In certain other of these embodiments, $R_2C(O-alkyl)_3$ is triethyl orthopropionate.

In certain embodiments of such methods, $H_2N$—$R_1$ is isobutylamine. In certain other embodiments, $H_2N$—$R_1$ is N-(4-aminobutyl)methanesulfonamide hydrochloride.

In certain embodiments, such methods further include: providing a mixture that includes isoamyl nitrite and a halogen source; combining the mixture and the compound of the formula:

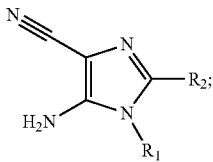

X' and heating the mixture comprising the compound of Formula X' to provide a compound of the formula:

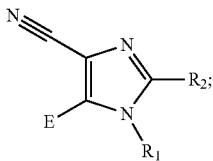

III' wherein: E is selected from the group consisting of —Cl, —Br, and —I.

Conditions of such reactions are described in greater detail hereinbelow.

In one embodiment, the present invention provides a compound of the formula:

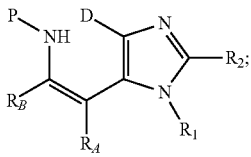

IV wherein:
D is selected from the group consisting of —C≡N, —C(O)—O—$C_{1-4}$alkyl, —C(O)—NH$_2$, —C(O)—H, —CH$_2$OH, and —CH$_2$O$C_{1-4}$alkyl;
P is selected from the group consisting of hydrogen, —C(O)—$C_{1-4}$alkyl, —C(O)—O—$C_{1-4}$alkyl, benzyl, and p-methoxybenzyl, or —NHP is replaced by a 2,5-dimethylpyrrole;
$R_A$ and $R_B$ taken together form a fused benzene ring or fused pyridine ring wherein the benzene ring or pyridine ring is unsubstituted or substituted by one or more R groups, or substituted by one $R_3$ group, or substituted by one $R_3$ group and one R group; wherein:
R is selected from the group consisting of:
halogen,
hydroxy,
alkyl,
haloalkyl,
alkoxy, and
—N($R_9$)$_2$;
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
$R_3$ is selected from the group consisting of:
—Z—$R_4$,
—Z—X—$R_4$,
—Z—X—Y—$R_4$,
—Z—X—Y—X—Y—$R_4$, and
—Z—X—$R_5$;
X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N═C($R_4$)—,
—C(═N—O—$R_8$)—,
—CH(—N(—O—$R_8$)-Q-$R_4$)—, $-\left(\begin{array}{c}N-Q-\\R_{10}\end{array}\right)$, $-N-C(R_6)-N-W-$, $R_7$ $-N-R_7-N-Q-$, $-V-N\left(\begin{array}{c}\\R^{10}\end{array}\right)$, and $R_7$ $-\left(\begin{array}{c}N-C(R_6)-N\\R_{10}\end{array}\right)$;

Z is a bond or —O—;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

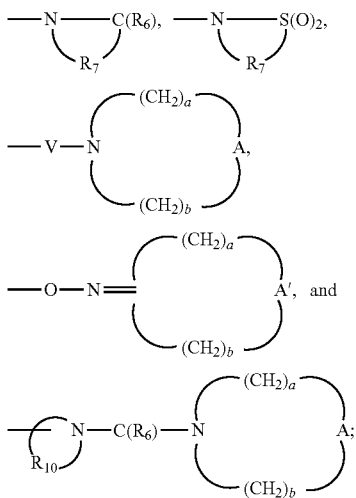

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, and —N(R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R)—N(R$_8$)—W—, —S(O)$_2$N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

In certain embodiments of such compounds, D is —C≡N.
In certain embodiments of such compounds, P is hydrogen.
For certain embodiments, including any one of the above embodiments of methods (i), (ii), and (iii), and compounds of Formula IV, $R_A$ and $R_B$ taken together form a fused benzene ring or fused pyridine ring wherein the benzene ring or pyridine ring is unsubstituted. In certain of these embodiments, $R_A$ and $R_B$ taken together form a fused benzene ring that is unsubstituted. In certain other embodiments, $R_A$ and $R_B$ taken together form a fused pyridine ring that is unsubstituted. In certain of these embodiments, the fused pyridine ring is

wherein the highlighted bond indicates the position where the ring is fused.

For certain embodiments, including any one of the above embodiments of methods (i), (ii), (iii), (iv), (v), and (vi), and compounds of Formula IV, $R_1$ is selected from the group consisting of —R$_{4a}$, —X$_a$—R$_4$, —X$_a$—Y—R$_4$, —X$_a$—Y—X—Y—R$_4$, and —X$_a$—R$_5$; $R_2$ is selected from the group consisting of —R$_{4a}$, —X$_a$—R$_4$, —X$_a$—Y—R$_4$, and —X$_a$—R$_5$; $X_a$ is selected from the group consisting of alkylene, alkenylene, alkynylene, arylene, and heteroarylene wherein the alkylene, alkenylene, and alkynylene groups can be optionally interrupted or terminated by arylene, heteroarylene or heterocyclylene and optionally interrupted by one or more —O— groups; and $R_{4a}$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, and alkynyl, oxo.

For certain embodiments, including any of the above embodiments of methods (i), (ii), (iv), (v), and (vi), and compounds of Formula IV, $R_1$ is selected from the group consisting of 2-methylpropyl, 2-hydroxy-2-methylpropyl, 2-(propylsulfonyl)ethyl, 2-methyl-2-[(methylsulfonyl)amino]propyl, 4-[(morpholin-4-ylcarbonyl)amino]butyl, and 4-methanesulfonylaminobutyl. For certain of these embodiments, $R_1$ is selected from the group consisting of 2-hydroxy-2-methylpropyl, 2-(propylsulfonyl)ethyl, 2-methyl-2-[(methylsulfonyl)amino]propyl, 4-[(morpholin-4-ylcarbonyl)amino]butyl, and 4-methanesulfonylaminobutyl. For certain of these embodiments, $R_1$ is 2-methylpropyl. For certain of these embodiments, $R_1$ is 4-methanesulfonylaminobutyl. For certain of these embodiments, particularly embodiments of methods (iv), (v), and (vi), $R_1$ is selected from the group consisting of 2-methylpropyl, 2-(propylsulfonyl)ethyl, 2-methyl-2-[(methylsulfonyl)amino]propyl, 4-[(morpholin-4-ylcarbonyl)amino]butyl, and 4-methanesulfonylaminobutyl. For certain of these embodiments, $R_1$ is 2-methylpropyl. For certain of these embodiments, $R_1$ is selected from the group consisting of 2-(propylsulfonyl)ethyl, 2-methyl-2-[(methylsulfonyl)amino]propyl, 4-[(morpholin-4-ylcarbonyl)amino]butyl, and 4-methanesulfonylaminobutyl. For certain of these embodiments, $R_1$ is 4-methanesulfonylaminobutyl.

For certain embodiments, including any of the above embodiments of methods (i), (ii), (iii), (iv), (v), and (vi), and compounds of Formula IV, $R_2$ is selected from the group consisting of hydrogen, methyl, ethyl, propyl, butyl, 2-methoxyethyl, 2-hydroxyethyl, ethoxymethyl, and hydroxymethyl. For certain of these embodiments, $R_2$ is selected from the group consisting of methyl, ethyl, propyl, butyl, 2-methoxyethyl, 2-hydroxyethyl, ethoxymethyl, and hydroxymethyl. For certain of these embodiments, $R_2$ is hydrogen. For certain of these embodiments, $R_2$ is ethyl. For certain of these embodiments, particularly embodiments of methods (iv), (v), and (vi), $R_2$ is selected from the group consisting of hydrogen, methyl, ethyl, propyl, butyl, 2-methoxyethyl, and ethoxymethyl. For certain of these embodiments, $R_2$ is hydrogen. For certain of these embodiments, $R_2$ is selected from the group consisting of methyl, ethyl, propyl, butyl, 2-methoxyethyl, and ethoxymethyl. For certain of these embodiments, $R_2$ is ethyl.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, and norbornenyl.

Unless otherwise specified, "alkylene", "alkenylene", and "alkynylene" refer to a divalent form of the "alkyl", "alkenyl", and "alkynyl" groups defined above. The terms, "alkylenyl", "alkenylenyl", and "alkynylenyl" are used when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" refer to a divalent form of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not.

The invention is inclusive of the compounds described herein in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

Preparation of the Compounds

More specific details of the reactions described herein are discussed in the context of the following schemes.

Some embodiments of the invention are described below in Reaction Schemes I through VII. For more detailed description of the individual reaction steps, see the EXAMPLES section below. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Although specific starting materials and reagents are depicted in the reaction schemes and discussed below, other starting materials and reagents known to those skilled in the art can be substituted to provide a variety of derivatives and/or reaction conditions. In addition, many of the methods described below can be further elaborated in light of this disclosure using conventional methods well known to those skilled in the art.

In carrying out methods of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, 3rd edition, John Wiley & Sons, New York, USA, 1999.

Conventional methods and techniques of separation and purification can be used to isolate compounds shown in the Reaction Schemes below. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

U.S. Pat. Nos. 5,268,376 (Gerster), 5,389,640 (Gerster et al.), 6,331,539 (Crooks et al.), 6,451,810 (Coleman et al.), 6,541,485 (Crooks et al.), 6,660,747 (Crooks et al.), 6,670,372 (Charles et al.), 6,683,088 (Crooks et al.), 6,656,938 (Crooks et al.), 6,664,264 (Dellaria et al.), 6,677,349 (Griesgraber), and 6,664,260 (Charles et al.). The reaction can be carried out by combining the compound of Formula XI and the carboxylic acid equivalent in a suitable solvent such as acetonitrile, tetrahydrofuran, nitromethane, water, diethyl ether, ethanol, methanol, or mixtures thereof and optionally heating, for example, at the reflux temperature of the solvent. The intermediate imidate can optionally be isolated before the addition of the primary amine. The reaction with the primary amine

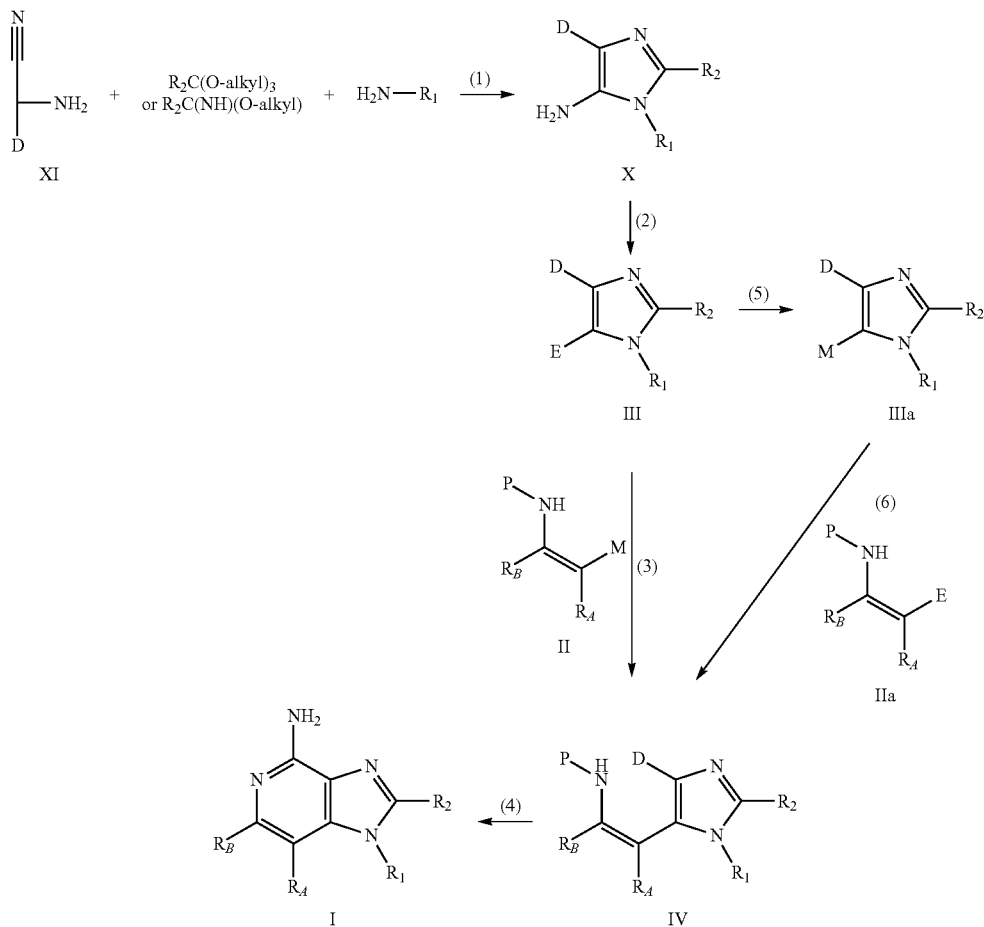

Reaction Scheme I

Methods of the invention are shown in Reaction Scheme I, wherein $R_1$, $R_2$, $R_A$, $R_B$, D, E, M, and P are as defined above. In step (1) of Reaction Scheme I, an α-amino-α-cyano-substituted compound of Formula XI reacts with a carboxylic acid equivalent and a primary amine or a salt thereof to provide an imidazole of Formula X. Many compounds of Formula XI have been shown to undergo this transformation, including, for example, ethyl 2-amino-2-cyanoacetate, 2-amino-2-cyanoacetamide, and aminomalononitrile. Suitable carboxylic acid equivalents include orthoesters of formula $R_2C(O\text{-alkyl})_3$ and alkyl imidates formula $R_2$—C(=NH)—O-alkyl. Numerous primary amines suitable for this reaction are commercially available; others can be prepared by known methods. See, for example, the methods in may be carried out at a temperature not lower than 0° C., and preferably the reaction may be carried out at an elevated temperature not higher than 120° C., and the product of Formula X or a salt thereof may be isolated by conventional methods.

Many compounds of Formula XI are commercially available as salts and need to be converted to the free base before the reaction shown in step (1) of Reaction Scheme I. Aminomalononitrile, wherein D is —C≡N, is a useful starting material for this reaction and is commercially available as its p-toluenesulfonate salt. Liberating the free amine has been carried out in the literature by bubbling dry ammonia through the solution to precipitate ammonium p-toluenesulfonate, which is filtered from the reaction mixture prior to the addition of the carboxylic acid equivalent; see Cristalli, G. et al, *J. Med. Chem.*, 34, pp. 1187-1192. An improved process for liberating the aminomalononitrile and carrying out step (1) is now reported, which does not require the filtration of the reaction mixture and does not require the handling of gaseous ammonia.

Step (1) can be conveniently carried out by combining aminomalononitrile with an orthoester of formula $R_2C(O\text{-alkyl})_3$ in the presence of one equivalent of a tertiary amine such as triethylamine or N,N-diisopropylethylamine and heating at an elevated temperature not higher than 120° C. Preferably, the reaction is typically carried out at a temperature not lower than 0° C. Preferably, the reaction is carried out at a temperature not lower than 25° C. Even more preferably, the reaction is carried out at a temperature not lower than 55° C. Preferably, the reaction is carried out at a temperature not greater than 80° C. The reaction is then cooled to a temperature at or below room temperature (and preferably to a temperature not lower than 0° C.) before the optional addition of a second equivalent of the tertiary amine and the addition of a primary amine of formula $R_1\text{—}NH_2$. Suitable solvents for this reaction include the solvents listed above as well as toluene. In some embodiments of the invention, step (1) of Reaction Scheme I can be carried out in toluene, and the product of Formula X precipitates from the reaction mixture and can easily be isolated by filtration.

Step (1) can also be carried out, in some embodiments of the invention, by combining aminomalononitrile with an orthoester of formula $R_2C(O\text{-alkyl})_3$ in the presence of one equivalent of pyridine and heating at an elevated temperature not higher than 120° C. Preferably, the temperature is not higher than 100° C. Preferably, the temperature is not lower than 75° C. The reaction is heated for a time sufficient to form the intermediate imidate, and then a primary amine of formula $R_1\text{—}NH_2$ is added at elevated temperature. Heating is continued to provide a compound of Formula X. Suitable solvents for this reaction include the solvents mentioned above for step (1).

In step (2) of Reaction Scheme I, an imidazole of Formula X is diazotized and dediazotized-substituted to form an imidazole of Formula III. The reaction can be carried out using a variety of well-known methods, by treating a primary amine with nitrous acid, a nitrite salt, or an alkyl nitrite in the presence of a nucleophile. For example, an amino-substituted imidazole of Formula X can be treated with sodium nitrite in the presence of cuprous iodide in fluoroboric acid at a temperature of, for example, –25° C. to provide a compound of Formula III, wherein E is iodide. Alternatively, the diazotization can be carried out by treating a compound of Formula X with tert-butyl nitrite in the presence of bromoform to provide a compound wherein E is bromide; the reaction can be carried out at room temperature or at an elevated temperature, for example, at the reflux temperature. The reaction is also known to take place by treating a solution of an amino-substituted imidazole in diiodomethane with isoamyl nitrite and heating at an elevated temperature in the range of 100° C. See, for example, Matsuda, A. et al, *J. Org. Chem.*, 64, pp. 7158-7152, (1999). Alternatively, diazotization can be followed by isolation of diazonium tetrafluoroborate salts to give compounds of Formula III wherein E is and $\text{—}N_2{}^+BF_4{}^-$. The reaction can be carried out by treating an amino-substituted imidazole of Formula X with sodium nitrite in aqueous fluoroboric acid or with an alkyl nitrite, such as tert-butyl nitrite, in the presence of excess boron trifluoride in an anhydrous solvent, such as dichloromethane, tetrahydrofuran, diethyl ether, or 1,2-dimethoxyethane (DME) at a sub-ambient temperature such as –25° C. to 10° C.

For compounds of Formula III wherein D is $\text{—}C\equiv N$, the present invention provides an improved diazotization and halogenation method that has been successfully used on large scale. The reaction can be conveniently carried out by pre-mixing a solution of isoamyl nitrite in diiodomethane or bromoform and optionally heating at an elevated temperature not higher than 110° C. The reaction is typically carried out at a temperature not lower than 50° C. Preferably, the reaction is carried out at a temperature not lower than 60° C. Preferably, the reaction is carried out at a temperature not greater than 90° C. Combining isoamyl nitrite and diiodomethane or bromoform can be carried out with a large excess of the halogenated reagent or with a moderate excess of reagent in the presence of a solvent. A solution of an amino-substituted imidazole of Formula X is then added, and the reaction is heated to provide a compound of Formula III. Suitable solvents for this method include chloroform, 1,2-dichloroethane, and acetonitrile. For some embodiments, the reaction in step (2) can be carried out by preheating a solution of isoamyl nitrite and iodine in a suitable solvent such as those listed above at an elevated temperature and then adding a solution of the imidazole of Formula X as described above. The use of iodine may be preferable to the use of diiodomethane, which in some reactions may be difficult to remove from the reaction mixture. If diiodomethane is used, excess diiodomethane may be removed at the end of the reaction by rotary evaporation.

In step (3) of Reaction Scheme I, a substituted imidazole of Formula III undergoes a transition-metal catalyzed cross coupling reaction with a reagent of Formula II or a salt thereof to form an imidazole-substituted aniline or aminopyridine of Formula IV. Several reagents of Formula II or their salts are commercially available, including 2-aminophenylboronic acid, 2-aminophenylboronic acid hydrochloride, and (2,2-dimethyl-N-[3-(4,4,5,5-tetramethyl-1,3,2-dioxaborolan-2-yl)pyridin-4-yl]propanamide; others can be prepared using methods described below in Reaction Scheme II.

Organoboron reagents wherein M is $\text{—}B(OH)_2$, $\text{—}B(O\text{-alkyl})_2$,

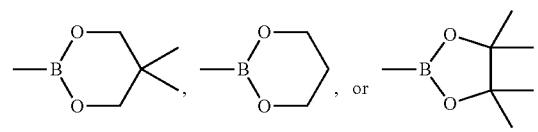

are known to undergo palladium-catalyzed cross-coupling with aryl halides and aryl triflates; this reaction is known as the Suzuki coupling. A Suzuki coupling can be conveniently carried out in step (3) of Reaction Scheme I by heating a mixture of a substituted imidazole of Formula III, palladium (II) acetate, triphenylphosphine, and an organoboron reagent of Formula II or a salt thereof in the presence of a base such as sodium carbonate. The reaction can be carried out in a suitable solvent or solvent mixture such as n-propanol:water and can be carried out at an elevated temperature, preferably at a temperature of at least 80° C., and preferably at a temperature no greater than 110° C.

The Suzuki coupling may also be carried out in step (3) of Reaction Scheme I by heating a substituted imidazole of Formula III, an organoboron reagent of Formula II, potassium phosphate, catalytic tris(dibenzylideneacetone)dipalladium (0)-chloroform adduct, and bis(2-diphenylphosphinophenyl) ether in a suitable solvent such as toluene. The reaction is typically carried out at an elevated temperature (preferably, at a temperature of at least 80° C., and preferably at a temperature of no greater than 120° C. and may optionally be carried out in the presence of powdered molecular sieves.

The Suzuki coupling in step (3) of Reaction Scheme I can also be conveniently carried out by heating a mixture of a substituted imidazole of Formula III, an organoboron reagent of Formula II or a salt thereof, potassium carbonate and catalytic dichlorobis(triphenylphosphine)palladium(II) in a suitable solvent or solvent mixture such as DME and water. The reaction can be carried out at an elevated temperature in the range of 80° C. to 120° C.

Suzuki couplings may be carried out under an inert atmosphere such as nitrogen or argon. Other palladium catalysts that may be used in the coupling reaction include tetrakis (triphenylphosphine)palladium(0), other palladium(0) complexes of this type with substituted phenyl groups, and allylpalladium chloride dimer. Bases other than sodium carbonate, potassium carbonate, or potassium phosphate that can be used in Suzuki couplings include, for example, triethylamine, sodium bicarbonate, cesium carbonate, sodium hydroxide, and barium hydroxide. These couplings may sometimes be carried out in the presence of tetrabutylammonium chloride. Suitable solvents other than toluene, n-propanol, and DME include benzene, acetone, N,N-dimethylformamide (DMF), and tetrahydrofuran, methanol and ethanol alone or in combination with toluene and/or water; N,N-dimethylacetamide (DMA), and 1,4-dioxane. Also, an aqueous solution of base can be used.

When E is —$N_2^+BF_4^-$, the Suzuki coupling in step (3) of Reaction Scheme I can be carried out without the addition of a base and at room temperature or at an elevated temperature, typically in the range of 20° C. to 70° C. Palladium catalysts that can be used for this reaction include but are not limited to palladium (II) acetate, palladium on carbon, and bis(dibenzylideneacetone)palladium. Suitable solvents for this transformation include but are not limited to methanol, water, dichloromethane, tetrahydrofuran, diethyl ether, 1,4-dioxane, and acetonitrile. The reaction can optionally be carried out in the presence of ligands such as triphenylphosphine or a thiourea such as that reported in Dai, M. et al., *Organic Letters*, 6, pp. 221-224, (2004).

Organostannane reagents wherein M is —$Sn(alkyl)_3$ are known to undergo palladium-catalyzed cross-coupling with aryl halides and aryl triflates; this reaction is known as the Stille coupling. The Stille coupling can be conveniently carried out by combining a substituted imidazole of Formula III with an organostannane of Formula II in the presence of a catalyst such as tetrakis(triphenylphosphine)palladium(0), $PhCH_2PdCl(PPh_3)_2$, $ArPdI(PPh_3)_2$, or dichlorobis(triphenylphosphine)palladium(II) in a suitable solvent such as DMF, dimethylsulfoxide, or N-methylpyrrolidone. The coupling can be carried out in the presence of lithium chloride, cesium fluoride, or tetramethylammonium fluoride and can be carried out at an elevated temperature (e.g., at a temperature of at least 40° C., and preferably no greater than 110° C.). When E is Cl or Br, the reaction may also be carried out by combining the imidazole with an organostannane of Formula II in the presence of catalytic palladium (II) chloride, catalytic copper (1) iodide, catalytic tributylplatinum, and cesium fluoride in DMF; see, Baldwin et al, *Angew. Chem.* 116, pp. 1152-1156, (2004).

Organozinc reagents, prepared as described below, wherein M is —Zn-Halide, are known to undergo transition metal-catalyzed cross-coupling with aryl halides and aryl triflates; this reaction is known as the Negishi coupling. The Negishi coupling can be conveniently carried out by combining a substituted imidazole of Formula III with an organozinc reagent of Formula II in the presence of a catalyst, typically a palladium or nickel catalyst such as tetrakis(triphenylphosphine)palladium(0), tetrakis(triphenylphosphine)nickel(0), dichlorobis(triphenylphosphine)nickel(II), or dichlorobis (triphenylphosphine)palladium(II) in a suitable solvent such as DMA, DMF, dimethylsulfoxide, or N-methylpyrrolidone. The coupling can be carried out in the presence of diisobutyl aluminum hydride and can be carried out at room temperature or an elevated temperature (e.g., at a temperature of at least 60° C., and preferably at a temperature of no greater than 100° C.).

The product of Formula IV or a pharmaceutically acceptable salt thereof, prepared by any of these coupling methods, can be isolated using conventional methods or may be used directly in step (4) without isolation.

In step (4) of Reaction Scheme I, a phenyl- or pyridyl-substituted imidazole of Formula IV undergoes cyclization to provide a 1H-imidazo[4,5-c]quinoline or 1H-imidazo[4,5-c] naphthyridine of Formula I. The present invention provides a variety of methods to effect the cyclization depending on the identity of D and P. These methods are described below in Reaction Schemes III through VI.

The present invention also provides an alternative route to a compound of Formula IV; this route is shown in steps (5) and (6) of Reaction Scheme I. In step (5) of Reaction Scheme I, a substituted imidazole of Formula III is converted to an organoborane, organostannane, or organozinc reagent of Formula IIIa. The conversion can be conveniently carried out when E is a halogen by halogen-lithium exchange and substitution. This reaction can be carried out under conditions similar to the lithiation-substitution conditions described in Reaction Scheme II below.

In step (6) of Reaction Scheme I, a substituted imidazole of Formula IIIa undergoes a transition-metal cross-coupling reaction with an aryl or heteroaryl halide or aryl or heteroaryl triflate of Formula IIa. The reaction conditions described for step (3) of Reaction Scheme I may be used. Several compounds of Formula IIa are commercially available. Others can be made by reduction of nitro-substituted halobenzenes or pyridines, for example, by heterogeneous hydrogenation in the presence of catalytic palladium on carbon or platinum on carbon in a suitable solvent, such as a lower alcohol (e.g., methanol, ethanol, isopropanol), acetonitrile, toluene, or mixtures thereof. Reduction of a nitro group can also be carried out using nickel boride, prepared in situ from sodium borohydride and nickel(II) chloride. The reduction can be conveniently carried out by adding a solution of a nitro-substituted halobenzene or pyridine in a suitable solvent or solvent mixture such as dichloromethane/methanol to a mixture of excess sodium borohydride and catalytic nickel(II) chloride in methanol. The reaction can be carried out at room temperature. Compounds of Formula IIa can also be prepared by carbamate or amide-directed lithiation and substitution with hexachloroethane or iodine according to the reaction conditions described in Reaction Scheme II.

Compounds of Formula IIa may be used to make compounds of Formula II. For example, organozinc reagents are typically prepared by reaction of a halogenated compound of Formula IIa with zinc dust in a suitable solvent such as DMA at an elevated temperature (e.g., at a temperature of at least 70° C., and preferably no greater than 90° C.) in the presence of catalytic iodine. Other methods for preparing compounds of Formula II are shown in Reaction Scheme II.

Reaction Scheme II

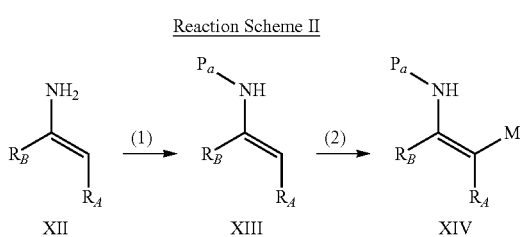

The preparation of compounds of Formula II is shown in Reaction Scheme II, wherein $R_A$, $R_B$, and M are as defined above, and $P_a$ is $(CH_3)_3C$—C(O)— or $(CH_3)_3C$—O—C(O)—. In step (1) of Reaction Scheme II, a substituted or unsubstituted aniline or aminopyridine of Formula XII is converted to a tert-butyl carbamate or a tert-butyl amide using conventional methods. For example, a tert-butyl carbamate is typically prepared by reacting of compound of Formula XII with di-tert-butyl dicarbonate optionally in the presence of a base, such as triethylamine, sodium hydroxide, sodium bis(trimethylsilyl)amide, or catalytic 4-dimethylaminopyridine. The reaction is typically carried out in a suitable solvent such as water, THF, ethyl acetate, or tert-butyl alcohol, and is usually successful at room temperature. A tert-butyl amide can be conveniently prepared by reacting of compound of Formula XII with pivaloyl chloride in the presence of a base, such as triethylamine, in a suitable solvent, such as THF. The reaction can be carried out at room temperature or below room temperature, for example, at a temperature of 0° C. to 20° C.

In step (2) of Reaction Scheme II, a carbamate- or amide-substituted benzene or pyridine of Formula XIII is converted to an organoborane or organostannane of Formula XIV. The transformation can be conveniently carried out using a lithiation-substitution reaction. tert-Butoxycarbonyl (Boc)- and pivaloyl-protected anilines undergo directed ortho metalation in the presence of butyllithium reagents. The resulting organolithium intermediate reacts with electrophiles such as B(O-alkyl)$_3$ and ClSn(alkyl)$_3$ to provide compounds of Formula XIV, where M is —B(O-alkyl)$_2$ and —Sn(alkyl)$_3$, respectively. Compounds of Formula XIV wherein M is —B(O-alkyl)$_2$ are readily hydrolyzed to compounds of Formula XIV wherein M is —B(OH)$_2$. The lithiation-substitution reaction can be conveniently carried out by treating a compound of Formula XIII with n-butyllithium or sec-butyllithium often in the presence of N,N,N,N-tetramethylethylenediamine and allowing the deprotonation to occur before the addition of the electrophile. Suitable solvents for the lithiation-substitution include ethers such as THF, diethyl ether, and tert-butyl methyl ether; hydrocarbons such as pentane, hexanes, heptanes, and octanes; aromatic solvents such as toluene, cumene, and xylenes; or mixtures thereof. The reaction can be carried out below room temperature, and preferably at a temperature not lower than −100° C. Preferably, the reaction is carried out at a temperature not higher than 0° C. More preferably, the reaction is carried out at a temperature not higher than −20° C. The reaction can conveniently be carried out at −78° C. The preparation of some compounds of Formula II has been reported in Rocca, P. et al, *Tetrahedron*, 49, pp. 49-64 (1993).

Other compounds of Formula II are available from the subset of Formula XIV using standard transformations. For example, a Boc group is typically removed by treatment with acid such as hydrochloric acid or trifluoroacetic acid in a suitable solvent such as ethanol. A compound of Formula II wherein P is hydrogen can then be converted to a compound wherein P is benzyl or substituted benzyl by reaction with benzyl chloride or a substituted benzyl chloride in the presence of a base such as triethylamine, potassium carbonate, or sodium carbonate in a suitable solvent such as water, ethanol, acetonitrile, or dichloromethane. The conversion of an amino group to a 2,5-dimethylpyrrole can also be carried out using conventional methods.

In Reaction Schemes III through VI below, various methods of converting a compound of Formula IV to a compound of Formula I are described. In these Reaction Schemes, $R_1$, $R_2$, $R_A$, $R_B$, E, M, and P are as defined above. For each of Reaction Schemes III through VI, step (1) is typically carried out by a transition-metal cross-coupling reaction as described in step (3) of Reaction Scheme I, and in step (2) an intramolecular cyclization of the product from the coupling reaction takes place to provide a 1H-imidazo[4,5-c]quinoline or 1H-imidazo[4,5-c]naphthyridine. When $R_A$ and $R_B$ join to form a pyridine ring, the cyclization often occurs under the conditions of the coupling reaction to provide a 1H-imidazo[4,5-c]naphthyridine. For some embodiments, the cyclization reaction is typically carried out under acidic conditions, and for some embodiments, the cyclization reaction is typically carried out under basic conditions. The cyclization conditions are governed by the identity of the P and D groups in a compound of Formula IV.

Reaction Scheme III

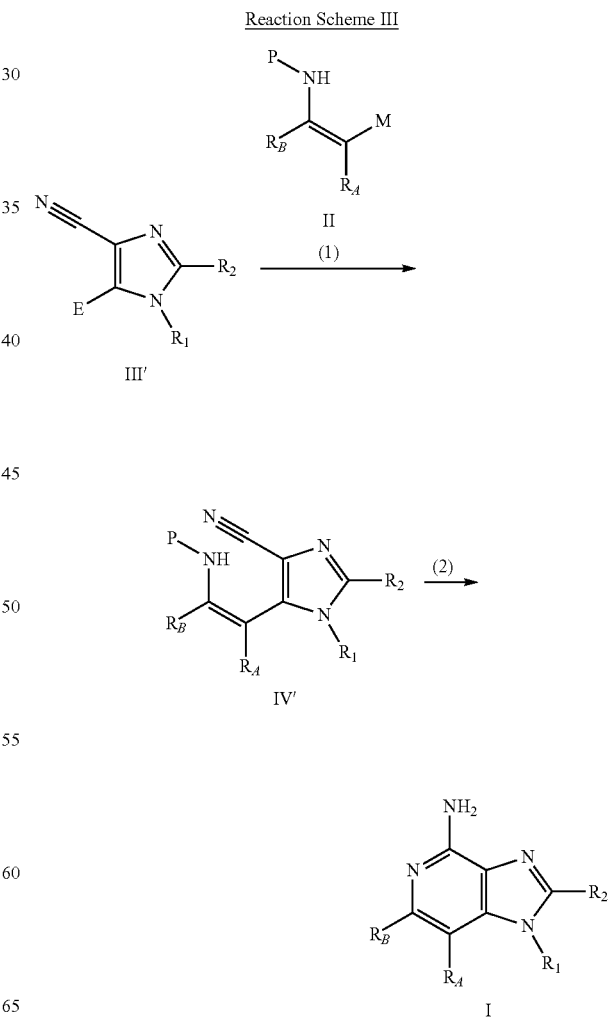

In step (2) of Reaction Scheme III, the amine and nitrile functionalities of a compound of Formula IV' wherein P is H or —C(O)—O—$C_{1-4}$alkyl react under acidic conditions to form a compound of Formula I. The intramolecular addition can be conveniently carried out by adding hydrogen chloride in a suitable solvent such as ethanol to the compound of Formula IV' and heating at a temperature not lower than 25° C. to provide the compound of Formula I. Preferably, the reaction is carried out at a temperature not lower than 50° C. The reaction can be conveniently carried out at the reflux temperature of the solvent, preferably at a temperature not lower than 70° C. Hydrogen chloride solutions are commercially available or can be readily prepared by stirring acetyl chloride in ethanol or by combining hydrogen chloride gas and a solvent such as ethanol. Under these acidic conditions, a Boc group is readily cleaved to provide a free amine, which undergoes the cyclization reaction. Other acids such as trifluoroacetic acid, sulfuric acid, phosphoric acid, acetic acid, and methanesulfonic acid may be used to effect the cyclization. Suitable solvents include but are not limited to lower alcohols (e.g. methanol, ethanol, n-propanol, isopropanol, tert-butanol); ethers such as diethyl ether, tetrahydrofuran, 1,4-dioxane; water; and combinations thereof. When P is benzyl or substituted benzyl, trifluoroacetic acid may be used at elevated temperatures (e.g., at a temperature of at least 50° C., and preferably at a temperature no greater than 100° C.) to remove the benzyl group and effect the cyclization.

In a compound of Formula IV' wherein P is —C(O)—$C_{1-4}$alkyl a base-promoted intramolecular cyclization in step (2) of Reaction Scheme III and cleavage of the $C_{1-4}$alkyl group take place to provide a compound of Formula I. The reaction can be conveniently carried out by heating the amide-substituted coupling product with potassium tert-butoxide in a suitable solvent such as ethanol at an elevated temperature, such as the reflux temperature of the solvent. Other bases that can be used for this transformation include sodium hydroxide, potassium carbonate, sodium carbonate, potassium bicarbonate, sodium bicarbonate, and ammonia, preferably in the form of ammonium hydroxide. Suitable solvents include but are not limited to lower alcohols, water; and combinations thereof.

Reaction Scheme IV

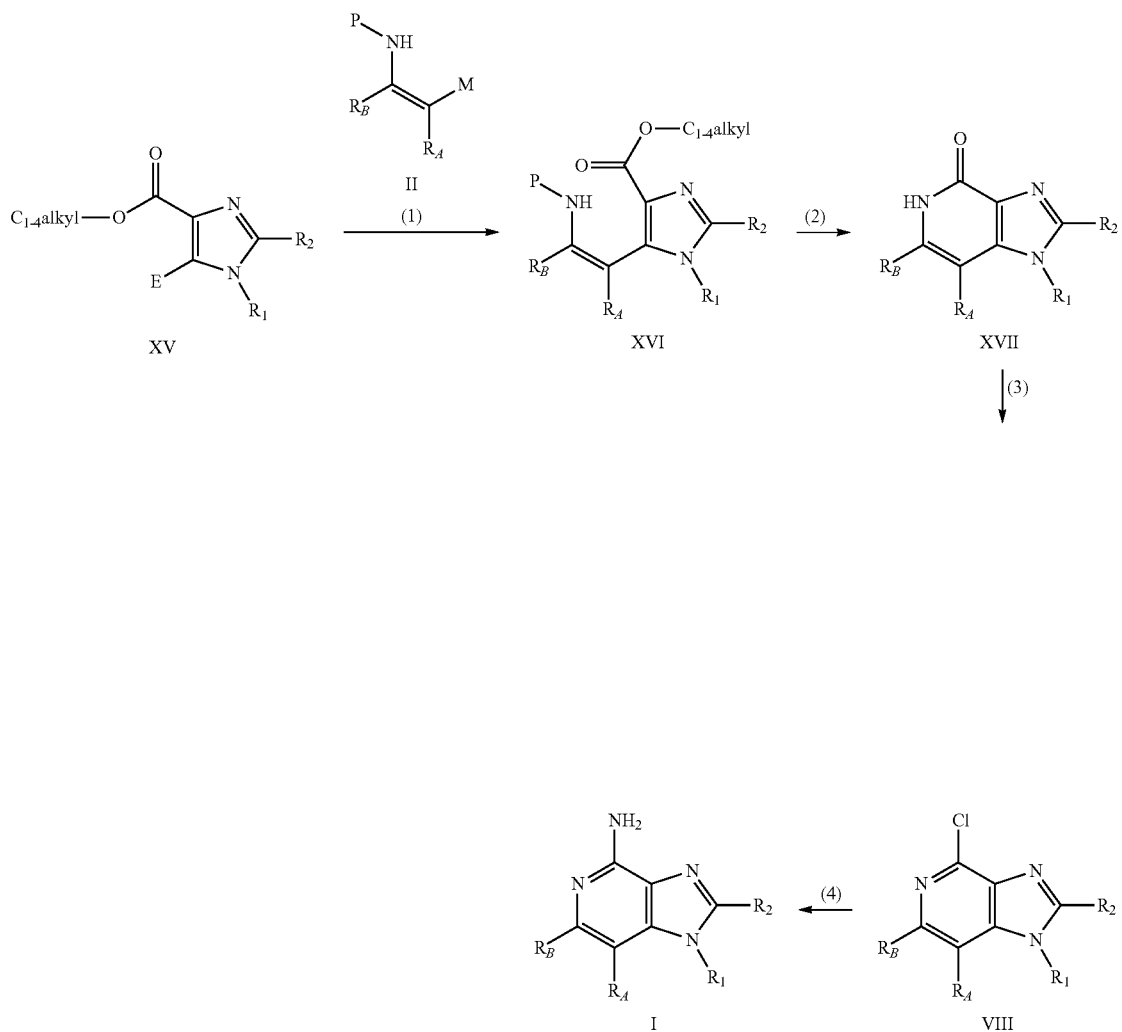

In Reaction Scheme IV, either the acidic or basic conditions described in step (2) of Reaction Scheme III can be used to provide a compound of Formula XVII from a compound of Formula XVI, depending on the identity of P. A compound of Formula XVII may also be obtained directly from the coupling reaction shown in step (1), particularly when P is hydrogen. In steps (3) and (4) of Reaction Scheme IV, a compound of Formula XVII is converted to a compound of Formula I. The two-step transformation can be carried out by chlorination and amination. The chlorination can be conveniently carried out by heating a compound of Formula XVII with excess phosphorus oxychloride. The reaction may be carried out at the reflux temperature (e.g., 100° C. to 110° C.). Other examples of chlorinating agents include, for example, thionyl chloride, phosgene, oxalyl chloride, diphenylphosphinic chloride, and phosphorus pentachloride. The reaction may be carried out in a solvent such as DMF, dichloromethane, acetonitrile, 1-methyl-2-pyrrolidinone (NMP), and 1,2-dichloroethane at room temperature or at an elevated temperature up to the reflux temperature, for example, at a temperature of 25° C. to 120° C. Amination of the 4-chloro compound of Formula VIII can be conveniently carried out by combining a solution of ammonia, for example, in a suitable solvent, such as methanol, with the 4-chloro compound and heating the mixture at an elevated temperature (e.g., not lower than 100° C., preferably not lower than 125° C., more preferably not lower than 140° C.). The reaction is preferably carried out at a temperature not higher than 200° C., more preferably not higher than 170° C. The amination may also be carried out by using ammonium acetate or ammonium hydroxide in combination with a compound of Formula VIII and heating.

step (3) of Reaction Scheme V, a compound of Formula XX is oxidized to a 5N-oxide of Formula XXI using a conventional oxidizing agent capable of forming N-oxides. The reaction can be conveniently carried out by adding 3-chloroperoxybenzoic acid to a solution of a compound of Formula XX in a solvent such as dichloromethane or chloroform. Alternatively, peracetic acid can be used as the oxidizing agent. The reaction with peracetic acid can be carried out in a suitable solvent such as ethanol at an elevated temperature such as 50° C. to 60° C.

In step (4) of Reaction Scheme V, a 5N-oxide of Formula XXI is aminated to provide a compound of Formula I. Step (4) can be carried out by the activation of an N-oxide of Formula XXI by conversion to an ester, for example, and then reacting the ester with an aminating agent. Suitable activating agents include, for example, alkyl- or arylsulfonyl chlorides such as benzenesulfonyl chloride, methanesulfonyl chloride, or p-toluenesulfonyl chloride. Suitable aminating agents include, for example, ammonia, in the form of ammonium hydroxide, for example, and ammonium salts such as ammonium carbonate, ammonium bicarbonate, and ammonium phosphate. The reaction can be conveniently carried out by adding ammonium hydroxide to a solution of the N-oxide of Formula XXI in a suitable solvent, such as dichloromethane or chloroform, and then adding p-toluenesulfonyl chloride. The reaction can be carried out at room temperature. The oxidation and amination steps may be carried out as a one-pot procedure without isolating the 5N-oxide of Formula XXI.

Alternatively, the 5N-oxide can be treated in step (4) with an isocyanate wherein the isocyanato group is bonded to a hydrolytically active functional group; subsequent hydrolysis

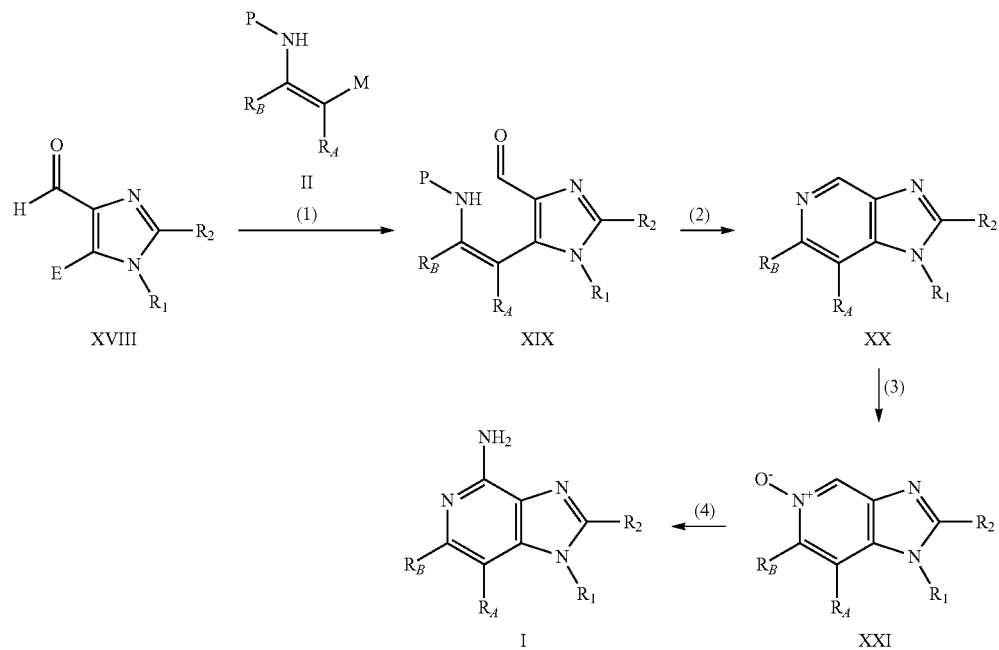

Reaction Scheme V

In Reaction Scheme V, either the acidic or basic conditions described in step (2) of Reaction Scheme III can be used to provide a compound of Formula XX from a compound of Formula XIX, depending on the identity of P. A compound of Formula XX may also be obtained directly from the coupling reaction shown in step (1), particularly when P is hydrogen. In of the resulting intermediate provides a compound of Formula I. Useful isocyanates include trichloroacetyl isocyanate. The reaction can be conveniently carried out in two steps. In step (i), trichloroacetyl isocyanate is combined with a solution of the N-oxide of Formula XXI in a solvent such as dichloromethane, and the mixture is typically stirred at room temperature to provide an isolable amide intermediate. In step (ii), a solution of the intermediate in methanol can be treated with a base such as sodium methoxide at room temperature.

Numerous acid chlorides, sulfonyl chlorides, sulfonic anhydrides, and isocyanates are commercially available; others can be readily prepared using known synthetic methods. The Reaction Scheme VI

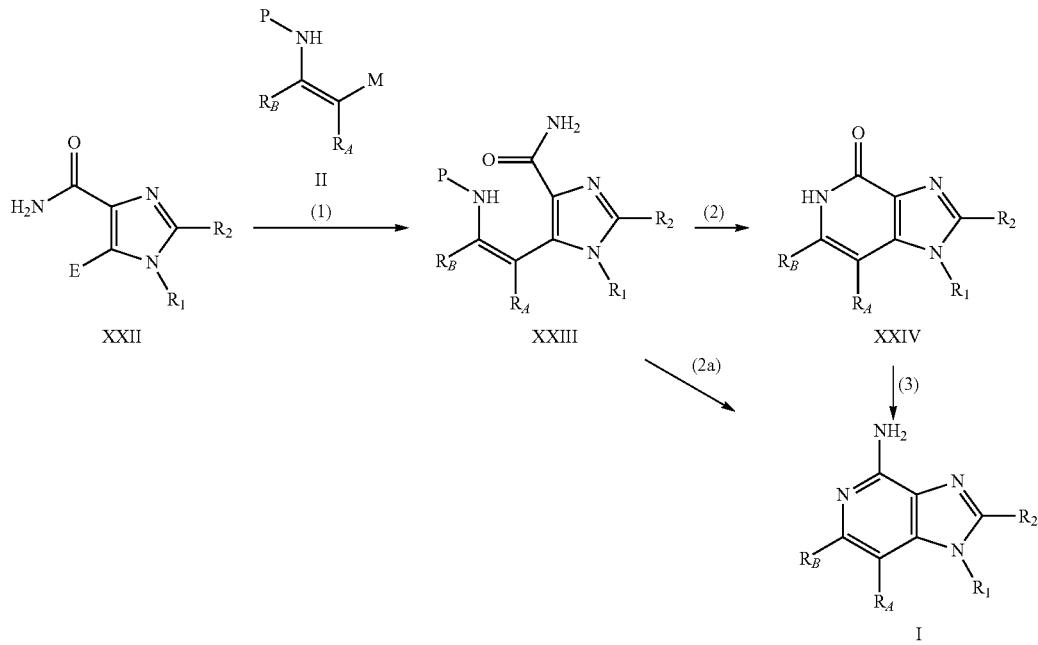

In Reaction Scheme VI, either the acidic or basic conditions described in step (2) of Reaction Scheme III can be used to provide a compound of Formula XXIV from a compound of Formula XXIII, depending on the identity of P. A compound of Formula XXIV may also be obtained directly from the coupling reaction shown in step (1), particularly when P is hydrogen. In step (3) of Reaction Scheme VI, a compound of Formula XXIV is converted to a compound of Formula I by using the chlorination and amination conditions described in steps (3) and (4) of Reaction Scheme IV. Alternatively, a compound of Formula I may be obtained directly from a compound of Formula XXIII as shown in step (2a) of Reaction Scheme VI using, for example, a dehydrating reagent during the cyclization. Step (2a) can be carried out by treating a compound of Formula XXIII with Lawesson's reagent in a mixture of THF and pyridine at an elevated temperature (e.g., at a temperature of at least 50° C., and preferably no greater than 70° C.).

For some embodiments, compounds shown in Reaction Scheme I can be further elaborated using conventional synthetic methods. Amines of Formula $R_1$—$NH_2$, used in step (1) of Reaction Scheme I, may contain a protected functional group, such as a tert-butoxycarbonyl-protected amino group. The protecting group installed in step (1) may be removed during or after the cyclization step shown in step (4) of Reaction Scheme I or in step (2) in each of Reaction Schemes III through VI to reveal, for example, an amino substituent on the $R_1$ group. An amino group introduced in this manner can react with an acid chloride of Formula $R_4C(O)Cl$, a sulfonyl chloride of Formula $R_4S(O)_2Cl$, a sulfonic anhydride of Formula $(R_4S(O)_2)_2O$, or an isocyanate of Formula $R_4N=C=O$ to provide a compound of Formula XX in which $R_1$ is —X—Y—$R_4$, where Y is —N($R_8$)-Q-, where $R_8$ is as defined above and Q is —C(O)—, —$SO_2$—, or —C(O)—NH—.

reaction can be conveniently carried out by adding the acid chloride, sulfonyl chloride, sulfonic anhydride, or isocyanate to a solution of a compound of Formula I, in which $R_1$ has an amino substituent, and a base such as triethylamine in a suitable solvent such as dichloromethane. The reaction can be carried out at room temperature. Functional groups can also be installed at $R_1$ using a variety of other known methods. See, for example, U.S. Pat. Nos. 4,689,338 (Gerster), 4,929,624 (Gerster et al.), 5,268,376 (Gerster), 5,389,640 (Gerster et al.), 6,331,539 (Crooks et al.), 6,451,810 (Coleman et al.), 6,541,485 (Crooks et al.), 6,660,747 (Crooks et al.), 6,670,372 (Charles et al.), 6,683,088 (Crooks et al.), 6,656,938 (Crooks et al.), 6,664,264 (Dellaria et al.), 6,677,349 (Griesgraber), and 6,664,260 (Charles et al.). Certain functional groups at the $R_1$ position may be protected during steps (1) and (2) of Reaction Scheme I. These functional groups include hydroxy groups. A hydroxy group can be conveniently protected as an ester, such as a methyl ester or an ethyl ester, using conventional methods.

For some embodiments, synthetic transformations can be made at the $R_2$ position in a compound of Formula I or III, if, for example, the carboxylic equivalent used in step (1) of Reaction Scheme I contains a protected hydroxy or amino group. Some carboxylic acid equivalents of this type are commercially available; others can be prepared by known synthetic methods. A protected hydroxy or amino group thus installed at the $R_2$ position can then be deprotected by a variety of methods well known to one of skill in the art. For example, hydroxyalkylenyl group is conveniently introduced at the $R_2$ position by the dealkylation of a methoxy- or ethoxyalkylenyl group, which can be installed by using a methoxy- or ethoxy-substituted carboxylic acid equivalent in step (1) of Reaction Scheme I. The dealkylation can be carried out by treating a compound of Formula III or Formula I wherein $R_2$ is an alkoxyalkylenyl group with boron tribromide in a suitable solvent such as dichloromethane at a sub-ambient temperature such as 0° C. The resulting hydroxy group may then be oxidized to an aldehyde or carboxylic acid or converted to a leaving group such as, for example, a chloro group using thionyl chloride or a trifluoromethanesulfonate group using trifluoromethanesulfonic anhydride. The resulting leaving group can then be displaced by a variety of nucleophiles. Sodium azide can be used as the nucleophile to install an azide group, which can then be reduced to an amino group using heterogeneous hydrogenation conditions. An amino group at the $R_2$ position can be converted to an amide, sulfonamide, sulfamide, or urea using the conventional methods described above. A leaving group at $R_2$, such as a chloro or trifluoromethanesulfonate group, can also be displaced with a secondary amine, a substituted phenol, or a mercaptan in the presence of a base such as potassium carbonate. For examples of these and other methods used to install a variety of groups at the $R_2$ position, see U.S. Pat. No. 5,389,640 (Gerster et al.). These synthetic transformations may conveniently be carried out as the last steps in the synthesis or prior to the coupling reaction.

For some embodiments, further synthetic manipulation of a compound prepared by Reaction Schemes I, III, IV, V, or VI can be carried out according to Reaction Scheme VII, wherein $R_1$ and $R_2$ are as defined above; n is 0 or 1; $R_d$ is selected from the group consisting of halogen, alkyl, alkenyl, trifluoromethyl, and dialkylamino; and $R_{3a}$ and $R_{3b}$ are defined below. In Reaction Scheme VII, particular D and P groups are shown in steps (1) and (2), but other D and P groups can be used following methods shown in Reaction Schemes III through VI. In step (1) of Reaction Scheme VII, a halogen-substituted imidazole carbonitrile of Formula XXV undergoes a transition-metal catalyzed cross coupling reaction with a reagent of Formula XXVI. Some compounds of Formula XXVI are known; see, Adams, L., *J. Heterocyclic Chem.*, 32, p. 1171 (1995). Others can be prepared by known synthetic methods such as those shown in Reaction Scheme II. The coupling reaction can be carried out as described in step (3) of Reaction Scheme I to provide a compound of Formula XXVIII.

In step (2) of Reaction Scheme VII, a pivaloylamino-substituted compound of Formula XXVIII undergoes a base-

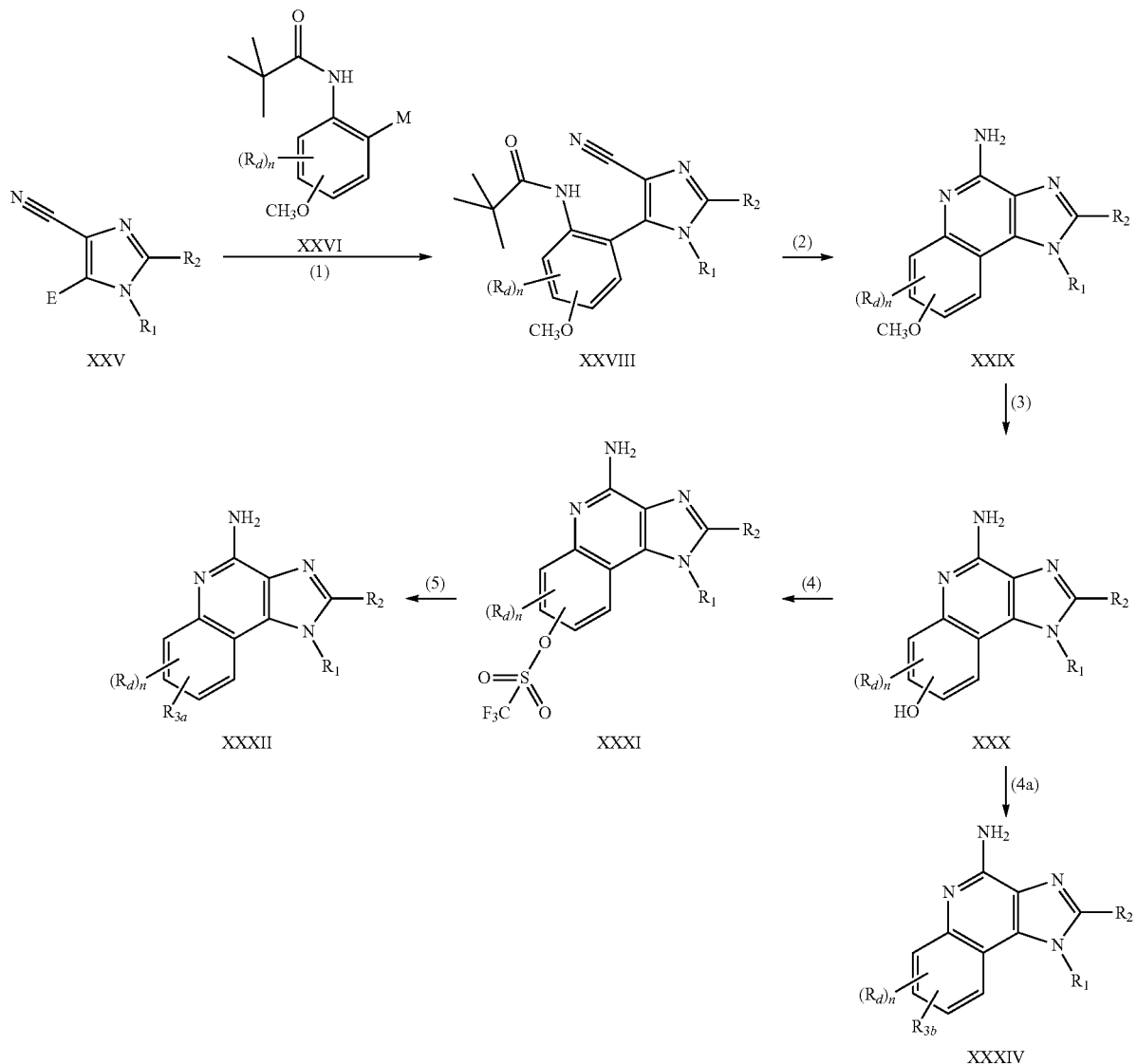

Reaction Scheme VII promoted intramolecular cyclization and subsequent cleavage of the pivaloyl group to provide a 1H-imidazo[4,5-c]quinolin-4-amine of Formula XXIX. The reaction can be carried out as described in step (2) of Reaction Scheme III.

In step (3) of Reaction Scheme VII, the methoxy group of a 1H-imidazo[4,5-c]quinolin-4-amine of Formula XXIX is demethylated to provide a hydroxy-substituted compound of Formula XXX. The demethylation can be conveniently carried out by treating the compound of Formula XXIX with a solution of boron tribromide, for example, in a suitable solvent, such as dichloromethane. The reaction can be carried out at a sub-ambient temperature (e.g., 0° C.). Alternatively, the demethylation can be carried out by heating the compound of Formula XXIX with anhydrous pyridinium chloride at an elevated temperature (e.g., 210° C.).

In step (4) of Reaction Scheme VII, the hydroxy group of a 1H-imidazo[4,5-c]quinolin-4-amine of Formula XXX is activated by conversion to a trifluoromethanesulfonate (triflate) group. The reaction can be conveniently carried out by treating a hydroxy-substituted compound of Formula XXX with N-phenyl-bis(trifluoromethanesulfonimide) in the presence of a tertiary amine such as triethylamine. The reaction can be carried out at room temperature in a suitable solvent such as DMF, and the triflate of Formula XXXI can be isolated using conventional methods. The activation in step (4) may also be accomplished by converting the hydroxy group to another good leaving group.

Step (5) of Reaction Scheme VII can be carried out using known palladium-catalyzed coupling reactions such as the Suzuki coupling, Heck reaction, the Stille coupling, and the Sonogashira coupling. For example, a triflate-substituted 1H-imidazo[4,5-c]quinolin-4-amine of Formula XXXI undergoes Suzuki coupling with a boronic acid of Formula $R_{3a}$—$B(OH)_2$, an anhydride thereof, or a boronic acid ester of Formula $R_{3a}$—$B(O\text{-alkyl})_2$; wherein $R_{3a}$ is —$R_{4b}$, —$X_e$—$R_4$, —$X_f$—Y—$R_4$, or —$X_f$—$R_5$; where $X_e$ is alkenylene; $X_1$ is arylene, heteroarylene, or alkenylene interrupted or terminated by arylene or heteroarylene; $R_{4b}$ is aryl or heteroaryl where the aryl or heteroaryl groups can be unsubstituted or substituted as defined in $R_4$ above; and $R_4$, $R_5$, and Y are as defined above. The reaction can be carried out as described in step (3) of Reaction Scheme I to provide a compound of Formula XXXII or a pharmaceutically acceptable salt thereof. Numerous boronic acids of Formula $R_{3a}$—$B(OH)_2$, anhydrides thereof, and boronic acid esters of Formula $R_{3a}$—$B(O\text{-alkyl})_2$ are commercially available; others can be readily prepared using known synthetic methods.

Alternatively, the Heck reaction can be used in step (5) of Reaction Scheme VII to provide compounds of Formula XXXII or a pharmaceutically acceptable salt thereof, wherein $R_{3a}$ is —$X_e R_{4b}$ or —$X_e$—Y—$R_4$, wherein $X_e$, Y, $R_4$, and $R_{1b}$ are as defined above. The Heck reaction is typically carried out by coupling a compound of Formula XXXI with a compound of the Formula $H_2C=C(H)$—$R_{4b}$ or $H_2C=C(H)$—Y—$R_4$. Several of these vinyl-substituted compounds are commercially available; others can be prepared by known methods. The reaction can be conveniently carried out by combining the compound of Formula XXXI and the vinyl-substituted compound in the presence of palladium (II) acetate, triphenylphosphine or tri-ortho-tolylphosphine, and a base such as triethylamine in a suitable solvent such as acetonitrile or toluene. The reaction can be carried out at an elevated temperature (e.g., at a temperature of at least 100° C., and preferably a temperature of no greater than 120° C.) under an inert atmosphere.

Compounds of Formula XXXII, wherein $R_{3a}$ is —$X_g$—$R_4$, $X_g$ is alkynylene, and $R_4$ is as defined above, can also be prepared by palladium catalyzed coupling reactions such as the Stille coupling or Sonogashira coupling. These reactions can be carried out by coupling a compound of Formula XXXI with a compound of the Formula $(\text{alkyl})_3\text{Sn}$—C≡C—$R_4$, $(\text{alkyl})_3\text{Si}$—C≡C—$R_4$, or H—C≡C—$R_4$.

Compounds of Formula XXXII prepared as described above by palladium-mediated coupling reactions, wherein $R_{3a}$ is —$X_e$—$R_4$, —$X_e$—Y—$R_4$, —$X_{f2}$—Y—$R_4$, —$X_{f2}$—$R_5$, or —$X_g$—$R_4$, where $X_{f2}$ is alkenylene interrupted or terminated by arylene or heteroarylene, and $X_e$, $X_g$, Y, $R_4$, and $R_5$ are as defined above, can undergo reduction of the alkenylene or alkynylene group present to provide compounds of Formula XXXII wherein $R_{3a}$ is —$X_h$—$R_4$, —$X_h$—Y—$R_4$, —$X_i$—Y—$R_4$, or —$X_i$—$R_5$, where $X_h$ is alkylene; $X_i$ is alkylene interrupted or terminated by arylene or heteroarylene; and $R_4$, $R_5$, and Y are as defined above. The reduction can be carried out by hydrogenation using a conventional heterogeneous hydrogenation catalyst such as palladium on carbon. The reaction can conveniently be carried out on a Parr apparatus in a suitable solvent, such as ethanol, methanol, or mixtures thereof.

In step (4a) of Reaction Scheme VII, a hydroxy-substituted 1H-imidazo[4,5-c]quinolin-4-amine of Formula XXX can be converted to a compound of Formula XXXIV, wherein $R_{3b}$ is —O—$R_4$, —O—X—$R_4$, —O—X—Y—$R_4$, or —O—X—$R_5$, and X, Y, $R_4$, and $R_5$ are as defined above, using a Williamson-type ether synthesis. The reaction can be effected by treating a hydroxy-substituted 1H-imidazo[4,5-c]quinolin-4-amine of Formula XXX with an aryl, alkyl, or arylalkylenyl halide of Formula Halide-$R_4$, Halide-alkylene-$R_4$, Halide-alkylene-Y—$R_4$, or Halide-alkylene-$R_5$ in the presence of a base. Numerous alkyl, arylalkylenyl, and aryl halides of these formulas are commercially available, including substituted benzyl bromides and chlorides, substituted or unsubstituted alkyl or arylalkylenyl bromides and chlorides, bromo-substituted ketones, esters, and heterocycles, and substituted fluorobenzenes. Other halides of these formulas can be prepared using conventional synthetic methods. The reaction can be conveniently carried out by combining an alkyl, arylalkylenyl, or aryl halide with the hydroxy-substituted compound of Formula XXX in a solvent such as DMF or DMA in the presence of a suitable base such as cesium carbonate. Optionally, catalytic tetrabutylammonium bromide can be added. The reaction can be carried out at ambient temperature or at an elevated temperature, for example, at 50° C. or 85° C., depending on the reactivity of the halide reagent. The methods described in International Patent Application Publication No. WO2005/020999 (Lindstrom et al.) and WO2005/032484 (Lindstrom et al.) can also be used.

The methods shown in Reaction Scheme VII can also be carried out to make substituted 1H-imidazo[4,5-c]naphthyridin-4-amine compounds by employing a substituted pyridine instead of a compound of Formula XXVI. In addition, a compound of Formula XXVI can be subjected to the methods of steps (3) through (5) or (4a) to provide elaborated organoborane or organostannane reagents, which can undergo coupling reactions according to the methods described in step (3) of Reaction Scheme I to provide compounds of Formula I.

EXAMPLES

Objects and advantages of this invention are further illustrated by the following examples, but the particular materials and amounts thereof recited in these examples, as well as other conditions and details, should not be construed to unduly limit this invention.

In the examples below automated flash chromatography on silica gel was carried out using a HORIZON HPFC system (an automated high-performance flash purification product available from Biotage, Inc, Charlottesville, Va., USA) or an INTELLIFLASH Flash Chromatography System (an automated flash purification system available from AnaLogix, Inc, Burlington, Wis., USA). The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Preparation of 5-Bromo-1,2-dimethyl-1H-imidazole-4-carbonitrile

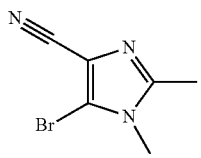

Part A

Dry ammonia was bubbled through a stirred solution of aminomalononitrile p-toluenesulfonate (30.0 g, 119 mmol) in anhydrous acetonitrile (800 mL). The reaction warmed slightly, and precipitate formed. The precipitate was removed by filtration, and the filtrate was concentrated to a volume of about 600 mL. Trimethyl orthoacetate (14.3 g, 119 mmol) was added, and the resulting solution was heated at reflux for 30 minutes and then allowed to cool to room temperature. N,N-Diisopropylethylamine (15.36 g, 119 mmol) and methylamine hydrochloride (8.03 g, 119 mmol) were sequentially added, and the resulting dark red solution was heated at reflux and then cooled to 0° C. Brown crystals formed and were isolated by filtration to provide 9 g of 5-amino-1,2-dimethyl-1H-imidazole-4-carbonitrile. The filtrate was concentrated under reduced pressure, and the resulting oil was triturated with 20% w/w aqueous sodium hydroxide to provide a yellow solid that was isolated by filtration provide 2 g of 5-amino-1,2-dimethyl-1H-imidazole-4-carbonitrile. The total yield of 5-amino-1,2-dimethyl-1H-imidazole-4-carbonitrile was 68%.

Part B

A solution of 5-amino-1,2-dimethyl-1H-imidazole-4-carbonitrile (8.5 g, 62 mmol) in bromoform (51 mL) was cooled with an ice water bath, and tert-butyl nitrite (12.87 g, 124.8 mmol) was added dropwise. The reaction was heated on a steam bath for 30 minutes, allowed to cool, and then refrigerated. The solution was decanted to separate it from a precipitate, and then the solution was purified by column chromatography on silica gel (eluting with ethyl acetate) to provide 5.2 g (42%) of 5-bromo-1,2-dimethyl-1H-imidazole-4-carbonitrile as a bright orange solid.

Preparation of 5-Bromo-2-butyl-1-(2-methylpropyl)-1H-imidazole-4-carbonitrile

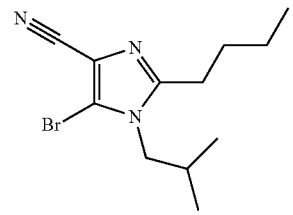

Part A

Dry ammonia was bubbled through a stirred solution of aminomalononitrile p-toluenesulfonate (25.0 g, 98.7 mmol) in anhydrous acetonitrile (1 L). The reaction warmed slightly, and precipitate formed. The precipitate was removed by filtration, and the filtrate was concentrated to a volume of about 500 mL. Trimethyl orthovalerate (17.0 mL, 98.7 mmol) was added, and the resulting solution was heated at reflux for 30 minutes and then allowed to cool to room temperature. Isobutylamine (9.8 mL, 99 mmol) was added, and the reaction was complete in minutes as evidenced by thin layer chromatography (TLC). The volatiles were removed under reduced pressure, and the residue was dissolved in ethyl acetate (400 mL). The resulting solution was washed sequentially with aqueous sodium hydroxide (75 mL of 2 M), water, and brine; dried over magnesium sulfate, and concentrated under reduced pressure to provide a dark solid. The crude product was purified by column chromatography on silica gel (eluting with 50/50 ethyl acetate/hexane) to provide 13.50 g (62%) of 5-amino-2-butyl-1-(2-methylpropyl)-1H-imidazole-4-carbonitrile as a brown solid.

Part B tert-Butyl nitrite (6.2 g, 0.060 mol) was added over a period of five minutes to solution of 5-amino-2-butyl-1-(2-methylpropyl)-1H-imidazole-4-carbonitrile (6.60 g, 30.0 mmol) in bromoform (50 mL). After about ten minutes, an exotherm occurred, and the reaction was poured into ice water. The reaction temperature peaked at 55° C. The reaction was stirred at room temperature for 45 minutes and then concentrated under reduced pressure while heating at about 55° C. The crude product (20 g) was purified by column chromatography on silica gel (eluting sequentially with dichloromethane and 5% ethyl acetate in dichloromethane) to provide 3.37 g (39%) of 5-bromo-2-butyl-1-(2-methylpropyl)-1H-imidazole-4-carbonitrile as an orange oil.

Preparation of 4-Aminopyridin-3-ylboronic acid hydrochloride salt

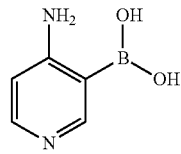

Part A

Under a nitrogen atmosphere, a solution of n-butyllithium in hexane (100 mL of 2.5 M, 250 mmol) was added over 20 minutes to a stirred solution of tert-butyl pyridin-4-ylcarbamate (19.4 g, 100 mmol) and N,N,N',N'-tetramethylethylenediamine (TMEDA) (31.4 g, 270 mmol) in tetrahydrofuran (THF) (500 mL) at −78° C. tert-Butyl pyridin-4-ylcarbamate is available from a literature procedure (Spivey, A. C. et al. *J. Org. Chem.* 1999, 64, 9430-9443). A white solid appeared and the mixture was stirred for 10 minutes at −78° C., was transferred to a salt bath, and allowed to warm slowly to −4° C. over about two hours before cooling to −78° C. again. Trimethyl borate (39.5 g, 380 mmol) was added over 15 minutes. The solution was warmed to 0° C. and poured into saturated aqueous ammonium chloride (500 mL). The mixture was stirred for 2 minutes. After standing at room temperature overnight, the mixture was partitioned between diethyl ether and brine. The organic layer was separated and washed with brine and then diluted to a volume of 3 liters with the addition of diethyl ether. A white solid formed in the organic layer and was isolated by filtration. The solid was washed sequentially with diethyl ether, water, and diethyl ether, then was dried to provide 17.1 g of 4-[(tert-butoxycarbonyl)amino]pyridin-3-ylboronic acid as a white solid.

Part B

Gaseous hydrogen chloride was combined with pure ethanol to provide a 3.6 M solution, which was added to 4-[(tert-butoxycarbonyl)amino]pyridin-3-ylboronic acid (2.4 g, 0.010 mol). Additional ethanol (10 mL) was added, and the reaction was heated at reflux for one hour with stirring and then allowed to cool to room temperature. The solvent was removed under reduced pressure to leave a volume of 5 mL of residue, which was poured into diethyl ether (150 mL) with stirring. A small volume of methanol was used to facilitate the transfer of material into the diethyl ether. A precipitate formed in the diethyl ether and was isolated by filtration and washed with diethyl ether to provide 1.65 g of 4-aminopyridin-3-ylboronic acid hydrochloride salt containing 7 mol % ethanol.

Example 1

Preparation of 5-(2-Aminophenyl)-1,2-dimethyl-1H-imidazole-4-carbonitrile

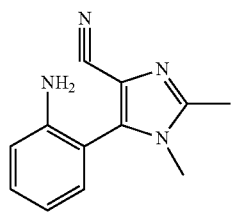

2-Aminophenylboronic acid (238 mg, 1.74 mmol), 5-bromo-1,2-dimethyl-1H-imidazole-4-carbonitrile (0.200 g, 1.00 mmol), and n-propanol (1.75 mL) were combined and placed under a nitrogen atmosphere. Palladium (II) acetate (134 μL of a 5 mg/mL solution in toluene, 0.003 mmol), triphenylphosphine (2.4 mg, 0.009 mmol), aqueous sodium carbonate (0.600 mL of 2 M) and water (0.350 mL) were added, and the vessel was evacuated and filled with nitrogen three times. The reaction was sealed and heated under a nitrogen atmosphere at 100° C. for four hours, allowed to cool to room temperature, further cooled with ice, and then partitioned between 2M aqueous sodium carbonate and dichloromethane. The aqueous layer was separated and extracted twice with chloroform. The combined organic fractions were dried over magnesium sulfate, filtered, and concentrated under reduced pressure to provide 210 mg of 5-(2-aminophenyl)-1,2-dimethyl-1H-imidazole-4-carbonitrile as a brown oil that crystallized upon standing.

Example 2

Preparation of 1,2-Dimethyl-1H-imidazo[4,5-c]quinolin-4-amine hydrochloride

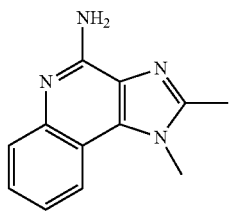

Under a nitrogen atmosphere, a solution of acetyl chloride (55 mg, 0.70 mmol) in ethanol (10 mL) was stirred for 10 minutes. 5-(2-Aminophenyl)-1,2-dimethyl-1H-imidazole-4-carbonitrile (0.100 g, 0.471 mmol) was added, and the reaction was heated at reflux under nitrogen for one hour and then allowed to cool to room temperature. A solid was present and was isolated by filtration, washed with diethyl ether, air-dried, and further dried under vacuum (6.65 Pa) at room temperature for 30 minutes to provide 89 mg (76%) of 1,2-dimethyl-1H-imidazo[4,5-c]quinolin-4-amine hydrochloride, which was found to have a $^1$H NMR spectrum consistent with the product.

Example 3

Preparation of 1,2-Dimethyl-1H-imidazo[4,5-c][1,6]naphthyridin-4-amine

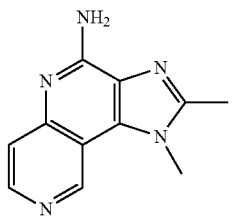

5-Bromo-1,2-dimethyl-1H-imidazole-4-carbonitrile (2.00 g, 10.0 mmol), palladium (II) acetate (112 mg, 0.499 mmol), triphenylphosphine (393 mg, 1.50 mmol), and water (3.5 mL) were added to a solution of 4-aminopyridin-3-ylboronic acid hydrochloride salt (3.5 g, 0.020 mol), aqueous sodium carbonate (17.5 mL of 2 M), and n-propanol (17.5 mL). The vessel was evacuated and filled with nitrogen three times. The reaction was sealed and heated under a nitrogen atmosphere at 100° C. for two hours and allowed to cool to room temperature. An analysis by high-performance liquid chromatography (HPLC) indicated the presence of starting material, and additional aqueous sodium carbonate (2.5 mL of 2M), palladium (II) acetate (56 mg), triphenylphosphine (197 mg), and 4-aminopyridin-3-ylboronic acid hydrochloride salt (872 mg) were added. The reaction was heated again at reflux for two hours, allowed to cool to room temperature, and further cooled with ice. A precipitate was present and was isolated by filtration and washed with water to provide 865 mg of 1,2-dimethyl-1H-imidazo[4,5-c][1,6]naphthyridin-4-amine. The product was purified by column chromatography on silica gel (eluting with 25% to 40% CMA in chloroform) to provide an analytically pure sample, mp 330-335° C.

Anal. Calcd. for $C_{11}H_{11}N_5$: C, 61.96; H, 5.20; N, 32.84. Found: C, 61.56; H, 5.17; N, 32.54.

Example 4

Preparation of 5-(2-Aminophenyl)-2-butyl-1-(2-methylpropyl)-1H-imidazole-4-carbonitrile

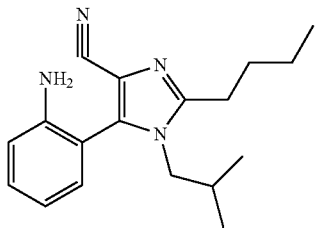

Palladium (II) acetate (5.0 mg, 0.022 mmol), triphenylphosphine (17 mg, 0.067 mmol), water (2.6 mL), n-propanol (13 mL), and aqueous sodium carbonate (4.4 mL of 2 M) were added to 2-aminophenylboronic acid (1.11 g, 8.13 mmol) and 5-bromo-2-butyl-1-(2-methylpropyl)-1H-imidazole-4-carbonitrile (2.10 g, 1.00 mmol). The reaction was placed under a nitrogen atmosphere and heated at 100° C. for 15 hours. An analysis by liquid chromatography/mass spectrometry (LC/MS) indicated the presence of starting material, and additional palladium (II) acetate (5.0 mg in 1 mL toluene) and triphenylphosphine (17 mg) were added. The reaction was heated at 100° C. for an additional 23.5 hours, and an analysis by LC/MS indicated the presence of starting material. Additional palladium (II) acetate (5.0 mg in 1 mL toluene), 2-aminophenylboronic acid (0.500 g), and aqueous sodium carbonate (2.2 mL of 2 M) were added, and the reaction was heated at reflux for an additional four hours and allowed to cool to room temperature. The reaction mixture was filtered to remove solid, and the filtrate was partitioned between 2M aqueous sodium carbonate and dichloromethane. The aqueous layer was separated and extracted twice with dichloromethane. The combined organic fractions were dried over magnesium sulfate, treated with decolorizing carbon, filtered, and concentrated under reduced pressure to provide 2.5 g of 5-(2-aminophenyl)-2-butyl-1-(2-methylpropyl)-1H-imidazole-4-carbonitrile as a brown solid. The solid was recrystallized from a mixture hexanes (30 mL) and tert-butyl methyl ether (20 mL) after hot filtration to provide 1.51 g of product. A portion (0.48 g) was recrystallized from a mixture of hexanes (6 mL) and tert-butyl methyl ether (6 mL) to provide 5-(2-aminophenyl)-2-butyl-1-(2-methylpropyl)-1H-imidazole-4-carbonitrile as a white solid.

Anal. Calcd. for $C_{18}H_{24}N_4$: C, 72.93; H, 8.16; N, 18.91. Found: C, 72.73; H, 8.47; N, 18.90.

Example 5

Preparation of 2-Butyl-1-(2-methylpropyl)-1H-imidazo[4,5-c]quinolin-4-amine hydrochloride

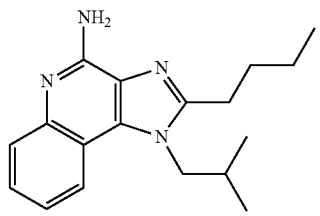

Under a nitrogen atmosphere, a solution of acetyl chloride (412 mg, 5.25 mmol) in anhydrous ethanol (17.5 mL) was stirred for 15 minutes. 5-(2-Aminophenyl)-2-butyl-1-(2-methylpropyl)-1H-imidazole-4-carbonitrile (1.04 g, 3.50 mmol) was added, and the reaction was heated at reflux under nitrogen for 21.5 hours, allowed to cool to room temperature overnight, and further cooled on an ice bath. A solid was present and was isolated by filtration, washed with diethyl ether, and air-dried to provide 1.04 g (89%) of 2-butyl-1-(2-methylpropyl)-1H-imidazo[4,5-c]quinolin-4-amine hydrochloride.

Anal. Calcd. for $C_{18}H_{25}N_4Cl$: C, 64.95; H, 7.57; N, 16.84; Cl, 10.65. Found: C, 64.70; H, 7.45; N, 16.74; Cl, 10.55.

Example 6

Preparation of 5-Amino-1-(2-methylpropyl)-2-propyl-1H-imidazole-4-carbonitrile

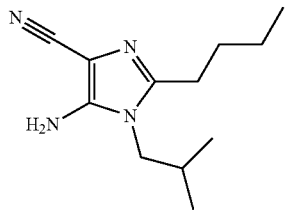

Aminomalononitrile p-toluenesulfonate (15.0 g, 59.2 mmol) and triethylamine (9.08 mL, 71.1 mmol) were combined in tetrahydrofuran (THF) (200 mL) and stirred for 30 minutes; the reaction became homogeneous. Trimethyl orthobutyrate (11.4 mL, 71.1 mmol) was added, and the solution was heated at reflux for three hours. An analysis by TLC indicated the presence of starting material, and additional trimethyl orthobutyrate (5.0 mL) was added. The solution was heated at reflux for another 3.5 hours and allowed to cool to room temperature. A mixture of isobutylamine (7.06 mL, 71.1 mmol) and triethylamine (9.08 mL, 71.1 mmol) was added, and the reaction was stirred overnight. The majority of the THF was removed under reduced pressure, and the residue was partitioned between dichloromethane and saturated aqueous sodium bicarbonate. The aqueous layer was extracted twice with dichloromethane. The combined organic fractions were washed with brine, dried over magnesium sulfate, and concentrated under reduced pressure to provide an orange solid that was triturated with ethyl acetate and isolated by filtration to provide 8.60 g (70%) of 5-amino-1-(2-methylpropyl)-2-propyl-1H-imidazole-4-carbonitrile as a white solid.

Example 7

Preparation of 5-Amino-1-(2-methylpropyl)-2-propyl-1H-imidazole-4-carbonitrile

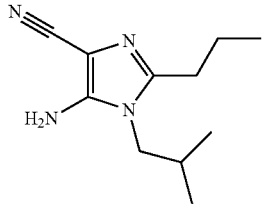

Aminomalononitrile p-toluenesulfonate (25.33 g, 0.100 mol), triethylamine (10.12 g, 0.100 mol), and trimethyl orthobutyrate (14.82 g, 0.11 mol) were combined in toluene (250 mL) and the solution was heated at 60° C. for 1.75 hours. Additional trimethyl orthobutyrate (1.0 mL) was added, and the reaction was allowed to cool over a period of 1.5 hours to 22° C. and further cooled to about 3° C. Triethylamine (10.12 g, 0.100 mol) and isobutylamine (7.32 g, 0.100 mol) were sequentially added, and the reaction was warmed to room temperature slowly and stirred overnight. The reaction mixture was shaken with 10% w/w aqueous sodium carbonate (250 mL), and the mixture was allowed to stand for two hours. A precipitate was present and was isolated by filtration, washed sequentially with toluene and water, air-dried, and further dried under vacuum at 75° C. for 22 hours to provide 14.5 g (70%) of 5-amino-1-(2-methylpropyl)-2-propyl-1H-imidazole-4-carbonitrile as a beige solid, mp 135.0-136.0° C.

Example 8

Preparation of 5-Amino-1-(2-methylpropyl)-2-propyl-1H-imidazole-4-carbonitrile

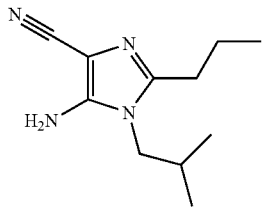

Aminomalononitrile p-toluenesulfonate (744.65 g, 2.94 mol), triethylamine (297.5 g, 2.94 mol), and trimethyl orthobutyrate (436 g, 2.94 mol) were combined in toluene (7.45 L) and the solution was heated at 60° C. for 2.5 hours. Additional trimethyl orthobutyrate (21 g) was added, and the reaction was allowed to cool over a period of 30 minutes, and triethylamine (297.5 g, 2.94 mol) was added. The solution was further cooled to about 3° C. over 30 minutes, and isobutylamine (215.03 g, 2.94 mol) was added over a period of 90 minutes. During the addition, the reaction temperature rose to 10° C. The reaction was warmed to room temperature slowly and stirred overnight. Deionized water (7.35 L) and sodium carbonate (735 g) were added over a period of 15 minutes while maintaining the temperature of the mixture at 20° C. with the addition of ice. The mixture was stirred for 15 minutes, and then the precipitate was isolated by filtration, washed sequentially with toluene (300 mL) and water (3 L), air-dried, and further dried under vacuum at 70° C. for 24 hours to provide 394.4 g (65%) of 5-amino-1-(2-methylpropyl)-2-propyl-1H-imidazole-4-carbonitrile as a beige solid, mp 134.5-136.5° C.

Example 9

Preparation of 5-Iodo-1-(2-methylpropyl)-2-propyl-1H-imidazole-4-carbonitrile

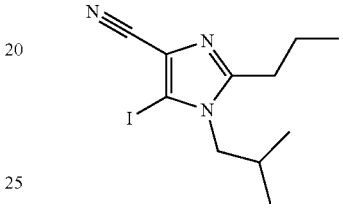

A solution of isoamylnitrite (6.1 mL, 45 mmol) and diiodomethane (20 mL) was heated at 85° C. under a nitrogen atmosphere. A solution of 5-amino-1-(2-methylpropyl)-2-propyl-1H-imidazole-4-carbonitrile (2.50 g, 12.1 mmol) in chloroform (60 mL) was added over a period of 30 minutes. The temperature reached 70° C. during the addition. The reaction was heated for an additional 15 minutes, allowed to cool to room temperature, and concentrated under reduced pressure. The residue was purified by suction filter chromatography on silica gel (eluting with a gradient of 10% to 25% ethyl acetate in hexane) to provide 2.88 g (75%) of 5-iodo-1-(2-methylpropyl)-2-propyl-1H-imidazole-4-carbonitrile as an orange oil that crystallized upon standing.

Example 10

Preparation of 5-Iodo-1-(2-methylpropyl)-2-propyl-1H-imidazole-4-carbonitrile

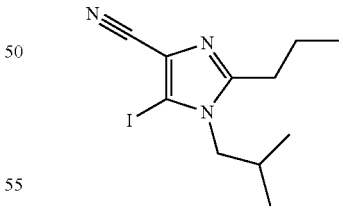

A solution of isoamylnitrite (106.3 g, 0.908 mol) and diiodomethane (1.296 kg, 4.84 mol) in chloroform (500 mL) was heated at 70° C. under a nitrogen atmosphere. A solution of 5-amino-1-(2-methylpropyl)-2-propyl-1H-imidazole-4-carbonitrile (50.0 g, 0.242 mol) in chloroform (500 mL) was heated to 70° C. was added over a period of 30 minutes while maintaining the reaction temperature at 68° C. to 70° C. during the addition. The reaction was heated for an additional 10 minutes, allowed to cool to room temperature, and concentrated under reduced pressure at 75° C. The residue was purified by column chromatography on silica gel (eluting sequentially with dichloromethane, 1% methanol in dichloromethane, 2% methanol in dichloromethane, and 3% methanol in dichloromethane) to provide 39.4 g (51.3%) of 5-iodo-1-(2-methylpropyl)-2-propyl-1H-imidazole-4-carbonitrile as a tan oil that solidified upon standing.

Example 11

Preparation of 5-Iodo-1-(2-methylpropyl)-2-propyl-1H-imidazole-4-carbonitrile

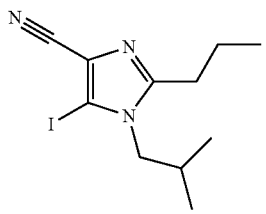

A solution of isoamylnitrite (21.3 g, 0.182 mol) and iodine (37.4 g, 0.147 mol) in acetonitrile (350 mL) was heated at 75° C. under a nitrogen atmosphere. A solution of 5-amino-1-(2-methylpropyl)-2-propyl-1H-imidazole-4-carbonitrile (10.0 g, 0.049 mol) in acetonitrile (350 mL) was heated to 50° C. was added slowly in portions while maintaining the reaction temperature at 75° C. to 77° C. during the addition. The reaction was heated for an additional 15 minutes and allowed to cool to room temperature. Diethyl ether (1.5 L) was added, and then sodium thiosulfite (100 g) in deionized water (500 mL) was added to the resulting solution with stirring. The mixture was stirred rapidly for 15 minutes. The organic layer was separated and washed with brine, dried over magnesium sulfate, filtered, and concentrated under reduced pressure to provide 16.18 g of an orange oil. The oil was purified by column chromatography on silica gel (eluting sequentially with 1% methanol in dichloromethane, 2% methanol in dichloromethane, 3% methanol in dichloromethane, and 4% methanol in dichloromethane) to provide 7.83 g (50.5%) of 5-iodo-1-(2-methylpropyl)-2-propyl-1H-imidazole-4-carbonitrile.

Example 12

Preparation of 5-(2-Aminophenyl)-1-(2-methylpropyl)-2-propyl-1H-imidazole-4-carbonitrile

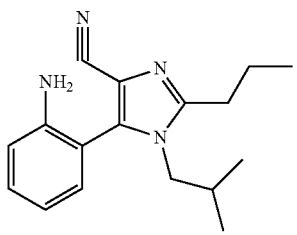

Triphenylphosphine (19 mg, 0.0735 mmol), water (2.9 mL), n-propanol (14.3 mL), aqueous sodium carbonate (9.8 mL of 2 M), and palladium (II) acetate (5.50 mg, 0.0245 mmol) were added to a mixture of 5-iodo-1-(2-methylpropyl)-2-propyl-1H-imidazole-4-carbonitrile (2.59 g, 8.17 mmol) and 2-aminophenylboronic acid hydrochloride (1.70 g, 9.80 mmol). The reaction vessel was evacuated and filled with nitrogen three times and then heated under nitrogen at 100° C. for 24 hours. The work-up procedure described in Example 4 was followed with the modification that the reaction mixture was partitioned between chloroform and brine, and the extractions of the aqueous fraction were carried out with chloroform. After the organic fractions were combined, 2.75 g of 5-(2-aminophenyl)-1-(2-methylpropyl)-2-propyl-1H-imidazole-4-carbonitrile were obtained as a brown solid.

Example 13

Preparation of 1-(2-Methylpropyl)-2-propyl-1H-imidazo[4,5-c]quinolin-4-amine

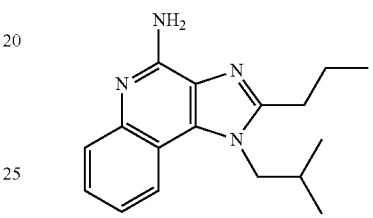

Under a nitrogen atmosphere, a solution of acetyl chloride (15 mmol) in anhydrous ethanol (50 mL) was stirred for 15 minutes and then added to 5-(2-aminophenyl)-1-(2-methylpropyl)-2-propyl-1H-imidazole-4-carbonitrile (2.75 g). The reaction was heated at reflux under nitrogen for 16 hours, allowed to cool to room temperature, and concentrated under reduced pressure. The residue was partitioned between 2M aqueous sodium carbonate and chloroform. The aqueous layer was separated and extracted twice with chloroform. The combined organic fractions were dried over magnesium sulfate, filtered, and concentrated under reduced pressure. The crude product (2.81 g) was purified by automated flash chromatography (eluting with 0% to 20% CMA in chloroform) and then recrystallized from acetonitrile (50 mL). The crystals were dried overnight at 33 Pa and 98° C. to provide 1.65 g of 1-(2-methylpropyl)-2-propyl-1H-imidazo[4,5-c]quinolin-4-amine as white needles, mp 191-192° C.

Anal. Calcd. for $C_{17}H_{22}N_4$: C, 72.31; H, 7.85; N, 19.84. Found: C, 72.22; H, 7.87; N, 19.83.

Example 14

Preparation of 1-(2-Methylpropyl)-2-propyl-1H-imidazo[4,5-c][1,6]naphthyridin-4-amine

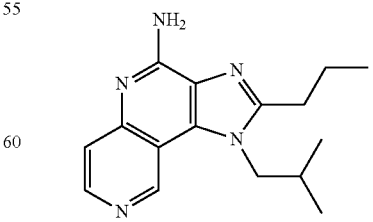

A solution of sodium carbonate (572 mg, 5.4 mmol) in deionized water (6 mL) was added to a solution of 5-iodo-1-(2-methylpropyl)-2-propyl-1H-imidazole-4-carbonitrile (634 mg, 2.0 mmol) and 4-aminopyridin-3-ylboronic acid hydrochloride salt (383 mg, 2.2 mmol) in n-propanol (15 mL), and nitrogen was bubbled through the resultant solution for 15 minutes. Palladium (II) acetate (22 mg, 0.1 mmol) and triphenylphosphine (79 mg, 0.3 mmol) were added. The reaction was evacuated and purged with nitrogen several times and then heated at reflux for 18 hours. The reaction mixture was partitioned between saturated aqueous sodium bicarbonate and ethyl acetate. The aqueous layer was separated and extracted several times with ethyl acetate. The combined organic fractions were washed with brine, dried over magnesium sulfate, filtered, and concentrated under reduced pressure. The crude product was purified by column chromatography on silica gel (eluting with 7% methanol in dichloromethane) to provide 210 mg of 1-(2-methylpropyl)-2-propyl-1H-imidazo[4,5-c][1,6]naphthyridin-4-amine as a tan solid.

Example 15

Preparation of tert-Butyl 2-[2-(5-amino-4-cyano-2-propyl-1H-imidazol-1-yl)ethoxy]ethylcarbamate

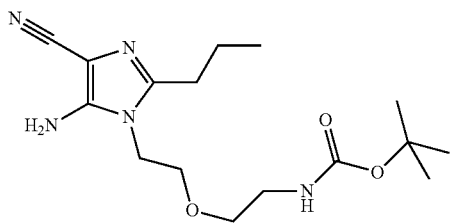

Part A

Under a nitrogen atmosphere, a solution of 2-(2-aminoethoxy)ethanol (27.8 mL, 277 mmol) in tetrahydrofuran (180 mL) was cooled to 0° C. Sodium hydroxide (140 mL of 2N) was added. A solution of di-tert-butyl dicarbonate (60.27 g, 277 mmol) in tetrahydrofuran (180 mL) was added dropwise over a period of 1 hour with rapid stirring. The reaction was allowed to warm to ambient temperature and stir overnight. The tetrahydrofuran was removed under reduced pressure. The pH of the resulting slurry was adjusted to ~3 by adding sulfuric acid (150 mL of 1M). The mixture was extracted with ethyl acetate (6×100 mL). The combined extracts were washed with water (2×100 mL) and brine (1×100 mL), dried over magnesium sulfate and then concentrated under reduced pressure to provide 48.53 g of tert-butyl 2-(2-hydroxyethoxy) ethylcarbamate as a colorless oil.

Part B

Under a nitrogen atmosphere, a solution of tert-butyl 2-(2-hydroxyethoxy)ethylcarbamate (48.53 g, 236 mmol) in anhydrous dichloromethane (1 L) was cooled to 0° C. Triethylamine (49.4 mL, 354 mmol)) was added. Methanesulfonyl chloride (20.10 mL, 260 mmol) was added dropwise over a period of 10 minutes. The reaction was allowed to warm to ambient temperature and stir overnight. The reaction was quenched with saturated sodium bicarbonate solution (500 mL). The organic layer was washed with water (3×500 mL) and brine (1×500 mL), dried over sodium sulfate and then concentrated under reduced pressure to provide 66.9 g of 2-{2-[(tert-butoxycarbonyl)amino]ethoxy}ethyl methanesulfonate as a brown oil.

Part C

Sodium azide (16.8 g, 259 mmol) was added to a solution of 2-{2-[(tert-butoxycarbonyl)amino]ethoxy}ethyl methanesulfonate (66.9 g, 236 mmol) in N,N-dimethylformamide (400 mL). The reaction was heated at 90° C. for 1.5 hours. The reaction mixture was allowed to cool to ambient temperature, diluted with cold water (500 mL) and then extracted with diethyl ether (4×300 mL). The combined extracts were washed with water (4×100 mL) and brine (1×200 mL), dried over magnesium sulfate and then concentrated under reduced pressure to provide 52 g of tert-butyl 2-(2-azidoethoxy)ethylcarbamate.

Part D

A solution of tert-butyl 2-(2-azidoethoxy)ethylcarbamate (52 g, 226 mmol) in methanol (500 mL) was added to a Parr vessel containing 10% palladium on carbon (4 g) which had been wetted with toluene (30 mL). The mixture was placed under hydrogen pressure (30 psi; $2.0 \times 10^5$ Pa). After 18.5 hours analysis by thin layer chromatography indicated that the reaction was not complete. Catalyst (0.5 g) was added and the hydrogenation was continued for an additional 4 hours. The reaction mixture was filtered through a layer of CELITE filter aid and a glass wool filter pad. The filter cake was rinsed with a mixture of isopropanol and methanol. The filtrate was concentrated under reduced pressure to provide tert-butyl 2-(2-aminoethoxy)ethylcarbamate.

Part E

Under a nitrogen atmosphere, aminomalononitrile p-toluenesulfonate (55.0 g, 0.217 mol) and anhydrous THF (1.1 L) were combined, and triethylamine (23.1 g, 0.228 mol) was added with stirring to the resulting suspension. After the suspension was stirred for 25 minutes; the reaction became homogeneous, and trimethyl orthobutyrate (36.5 mL, 0.228 mol) was added. The solution was heated at reflux for 75 minutes. An analysis by TLC indicated the presence of starting material, and additional trimethyl orthobutyrate (3.5 mL) was added. The solution was heated at reflux for another 15 minutes and allowed to cool to 25° C. Triethylamine (32 mL, 0.29 mol) and tert-butyl 2-(2-aminoethoxy)ethylcarbamate (48.8 g, 0.239 mol) were added, and the reaction was stirred for 18 hours at room temperature. The volatiles were removed under reduced pressure, and the residue was partitioned between dichloromethane (1 L) and saturated aqueous sodium bicarbonate (250 mL). The organic layer was separated and washed sequentially with saturated aqueous sodium carbonate (250 mL) and brine (250 mL), dried over sodium sulfate, filtered, and concentrated under reduced pressure. The residue was combined with material from another run and purified by column chromatography on silica gel (eluting with 20% ethyl acetate in hexane) to provide 67 g (77%) of tert-butyl 2-[2-(5-amino-4-cyano-2-propyl-1H-imidazol-1-yl)ethoxy]ethylcarbamate as an orange semi-solid.

Example 16

Preparation of tert-Butyl 2-[2-(4-cyano-5-iodo-2-propyl-1H-imidazol-1-yl)ethoxy]ethylcarbamate

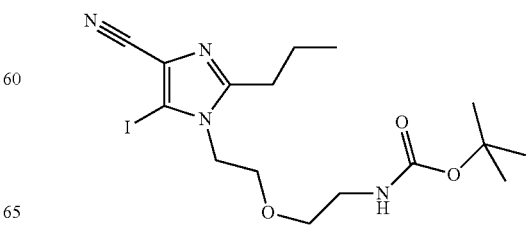

A solution of isoamylnitrite (96 mL, 715 mmol), diiodomethane (475 mL), and chloroform (240 mL) was heated to 80° C. over a period of one hour. A solution of tert-butyl 2-[2-(5-amino-4-cyano-2-propyl-1H-imidazol-1-yl)ethoxy]ethylcarbamate (64.3 g, 191 mmol) in chloroform (240 mL) was added dropwise over a period of 115 minutes. During the addition the reaction temperature was decrease to 74° C. The reaction was allowed to cool to 50° C., and the chloroform was removed under reduced pressure. The resulting liquid was diluted with a small volume of dichloromethane and was purified by chromatography on silica gel (eluting sequentially with hexanes and ethyl acetate) and dried under high vacuum at 60° C. for eight hours to provide 56.3 g (66%) of tert-butyl 2-[2-(4-cyano-5-iodo-2-propyl-1H-imidazol-1-yl)ethoxy]ethylcarbamate as a dark orange oil containing a small amount of diiodomethane.

Example 17

Preparation of 5-Amino-1-(2-methylpropyl)-1H-imidazole-4-carbonitrile

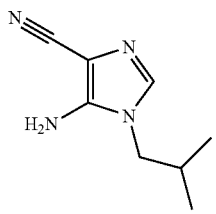

Aminomalononitrile p-toluenesulfonate (2.2 g, 8.7 mmol) and THF (45 mL) were combined, and triethylamine (1.3 mL, 9.9 mmol) was added with stirring to the resulting suspension. After the suspension was stirred for 30 minutes, the reaction became homogeneous, and trimethyl orthoformate (1.0 mL, 9.1 mmol) was added. The solution was heated to reflux over a period of about two hours and then heated at reflux for three hours. An analysis by TLC indicated the presence of starting material, and additional trimethyl orthoformate (1.0 mL) was added. The solution was heated at reflux for another two hours and allowed to cool to room temperature. Triethylamine (1.0 g, 9.9 mmol) and isobutylamine (1.5 g, 0.020 mol) were added in rapid succession, and the reaction was stirred overnight at room temperature. The volatiles were removed under reduced pressure, and the residue was dissolved in dichloromethane (50 mL). The resulting solution was washed with saturated aqueous sodium carbonate (50 mL). The aqueous layer was separated and extracted with dichloromethane. The combined organic fractions were washed with saturated aqueous sodium carbonate, and the aqueous fraction was separated and extracted with dichloromethane. The combined organic fractions were washed with brine (250 mL); solids at the interface were included in the organic fraction. Methanol was added to the organic fraction to dissolve the solids. The solution was dried over sodium sulfate, filtered, and concentrated under reduced pressure to provide 1 g (70%) product. The product was combined with material from another run and purified by automated flash chromatography (eluting with 0 to 20% CMA in chloroform) to provide 0.7 g (54%) of 5-amino-1-(2-methylpropyl)-1H-imidazole-4-carbonitrile as a light brown solid, mp 186-188° C.

Example 18

Preparation of 5-Iodo-1-(2-methylpropyl)-1H-imidazole-4-carbonitrile

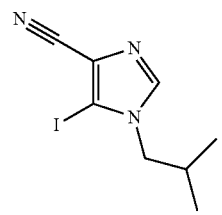

A solution of isoamylnitrite (0.27 g, 2.3 mmol), diiodomethane (1 mL), and chloroform (5 mL) was heated at 85° C. under a nitrogen atmosphere. A mixture of 5-amino-1-(2-methylpropyl)-1H-imidazole-4-carbonitrile (0.1 g, 0.6 mmol) and chloroform (5 mL) was added over a period of 15 minutes followed by a rinse with chloroform (2 mL). The reaction was stirred and heated at 80° C. for an additional 10 minutes, allowed to cool to room temperature, and concentrated under reduced pressure. The residue was purified through a layer of silica gel (eluting sequentially with chloroform, 2% methanol in chloroform, 4% methanol in chloroform, and 8% methanol in chloroform) to provide 0.15 g (90%) of 5-iodo-1-(2-methylpropyl)-1H-imidazole-4-carbonitrile as an orange solid.

Example 19

Preparation of 5-(2-Aminophenyl)-1-(2-methylpropyl)-1H-imidazole-4-carbonitrile

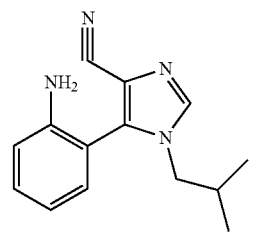

A solution of 5-iodo-1-(2-methylpropyl)-1H-imidazole-4-carbonitrile (0.15 g, 0.54 mmol) in 1,2-dimethoxyethane (DME) (6 mL) and then water (3 mL) were added to a mixture of 2-aminophenylboronic acid hydrochloride (0.21 g, 1.2 mmol) and potassium carbonate (0.27 g, 1.9 mmol), and the mixture was evacuated and purged with nitrogen three times. Dichlorobis(triphenylphosphine)palladium(II) (16 mg, 0.02 mmol) was added, and the mixture was flushed with nitrogen and heated at reflux (90° C.) for one hour and allowed to cool to room temperature. The reaction mixture was filtered through a layer of CELITE filter aid, and the filter cake was washed with water (30 mL) and dichloromethane (40 mL). The filtrate layers were separated, and the aqueous layer was extracted with dichloromethane (20 mL). The combined organic fractions were concentrated under reduced pressure, and the residue was purified by column chromatography on silica gel to provide 0.13 g of 5-(2-aminophenyl)-1-(2-methylpropyl)-1H-imidazole-4-carbonitrile as an amber liquid that crystallized upon standing for 20 minutes.

Example 20

Preparation of 1-(2-Methylpropyl)-1H-imidazo[4,5-c]quinolin-4-amine hydrochloride

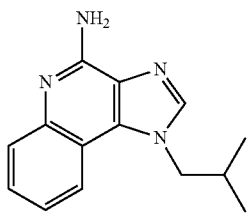

A solution of acetyl chloride (0.15 mL, 2 mmol) in ethanol (2 mL) was added to a solution of 5-(2-aminophenyl)-1-(2-methylpropyl)-1H-imidazole-4-carbonitrile (0.13 g) in ethanol (5 mL). The mixture was heated at reflux for two hours and allowed to cool to ambient temperature. The volume of the mixture was decreased to 2 mL by concentrating under reduced pressure. A solid was present, and the remaining liquid was decanted away from the solid, which was washed with diethyl ether (2×2 mL) and dried overnight in a vacuum oven at room temperature to provide 0.035 g (23% for Example 19 and Example 20 combined) of 1-(2-methylpropyl)-1H-imidazo[4,5-c]quinolin-4-amine hydrochloride as a beige solid, mp>265° C.

Anal. Calcd. for $C_{14}H_{17}N_4Cl$: C, 60.76; H, 6.19; N, 20.24. Found: C, 60.93; H, 5.81; N, 20.06.

Example 21

Preparation of N-[4-(5-Amino-4-cyano-2-ethyl-1H-imidazol-1-yl)butyl]methanesulfonamide

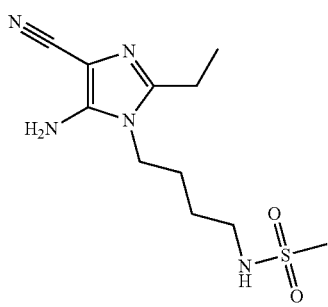

Aminomalononitrile p-toluenesulfonate (2.0 g, 7.9 mmol) and THF (40 mL) were combined, and triethylamine (1.2 mL, 8.7 mmol) was added with stirring to the resulting suspension. After the suspension was stirred for 30 minutes, the reaction became homogeneous, and triethyl orthopropionate (1.5 g, 8.7 mmol) was added. The solution was heated at reflux for one hour. An analysis by TLC indicated the presence of starting material, and additional triethyl orthopropionate (0.2 mL) was added. The solution was heated at reflux for another two hours and allowed to cool to room temperature. Triethylamine (1.2 mL, 8.7 mmol) was then added followed quickly by the supernatant portion of a mixture of 4-aminobutylmethanesulfonamide hydrochloride (see Example 199 in U.S. Patent Application Publication No. 2004/0147543, 1.75 g, 8.7 mmol), triethylamine (1.2 mL, 8.7 mmol), and THF (10 mL) that had been stirred for about 1.5 hours. The reaction was stirred overnight at room temperature. An analysis by TLC indicated the presence of starting material, and a mixture of 4-aminobutylmethanesulfonamide hydrochloride (1.0 g), triethylamine (0.8 mL), and dichloromethane (15 mL) was added. The reaction was stirred at room temperature for another seven hours. The volatiles were removed under reduced pressure, and the residue was dissolved in dichloromethane (40 mL). The resulting solution was washed with saturated aqueous sodium carbonate (40 mL) and brine, dried over sodium sulfate, filtered, and concentrated under reduced pressure to provide 1.34 g of an amber syrup. The syrup was purified by automated flash chromatography (eluting with 0 to 40% CMA in chloroform) to provide 0.21 g (9%) of N-[4-(5-amino-4-cyano-2-ethyl-1H-imidazol-1-yl)butyl]methanesulfonamide as a glassy, amber solid.

Example 22

Preparation of N-[4-(4-Cyano-2-ethyl-5-iodo-1H-imidazol-1-yl)butyl]methanesulfonamide

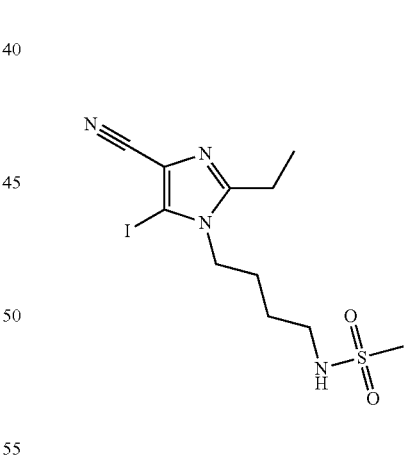

A solution of isoamylnitrite (0.30 g, 2.6 mmol), diiodomethane (2 mL), and chloroform (3 mL) was heated at 85° C. A mixture of N-[4-(5-amino-4-cyano-2-ethyl-1H-imidazol-1-yl)butyl]methanesulfonamide (0.2 g, 0.7 mmol) and chloroform (8 mL) was added over a period of 15 minutes. The reaction was stirred and heated at 80° C. for an additional 10 minutes, allowed to cool to room temperature, and concentrated under reduced pressure. The residue was purified through a layer of silica gel (15 g, eluting sequentially with chloroform, 2% methanol in chloroform, 4% methanol in chloroform, 8% methanol in chloroform, and 10% methanol in chloroform) to provide 0.16 g (57%) of N-[4-(4-cyano-2-ethyl-5-iodo-1H-imidazol-1-yl)butyl]methanesulfonamide as an amber syrup.

Example 23

Preparation of N-{4-[5-(2-Aminophenyl)-4-cyano-2-ethyl-1H-imidazol-1-yl]butyl}methanesulfonamide

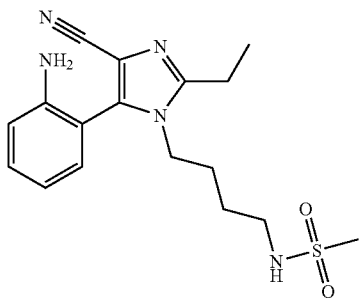

A solution of N-[4-(4-cyano-2-ethyl-5-iodo-1H-imidazol-1-yl)butyl]methanesulfonamide (0.16 g, 0.4 mmol) in DME (6 mL) and then water (3 mL) were added to a mixture of 2-aminophenylboronic acid hydrochloride (0.11 g, 0.8 mmol) and potassium carbonate (0.18 g, 1.3 mmol), and the resulting orange solution was evacuated and purged with nitrogen three times.

Dichlorobis(triphenylphosphine)palladium(II) (6 mg, 0.01 mmol) was added, and the mixture was flushed with nitrogen and heated at reflux (90° C.) for one hour and allowed to cool to room temperature. The reaction mixture was filtered through a layer of CELITE filter aid, and the filter cake was washed with water (40 mL) and dichloromethane (40 mL). The filtrate layers were separated, and the aqueous layer was extracted with dichloromethane (2×15 mL). The combined organic fractions were concentrated under reduced pressure, and the residue was purified by column chromatography on silica gel to provide 0.19 g of N-{4-[5-(2-aminophenyl)-4-cyano-2-ethyl-1H-imidazol-1-yl]butyl}methanesulfonamide as pale orange syrup.

Example 24

Preparation of N-[4-(4-Amino-2-ethyl-1H-imidazo[4,5-c]quinolin-1-yl)butyl]methanesulfonamide

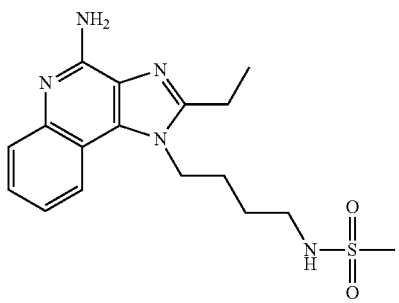

A solution of acetyl chloride (0.15 mL, 2 mmol) in ethanol (2 mL) was added to a solution of N-{4-[5-(2-aminophenyl)-4-cyano-2-ethyl-1H-imidazo 1-yl] butyl}methanesulfonamide (0.19 g) in ethanol (4 mL). The mixture was heated at reflux for two hours, allowed to cool to room temperature, and concentrated under reduced pressure. The resulting off-white solid was dissolved in water (2.0 mL) with heating to 60° C. The resulting solution was adjusted to pH 12 with the addition of 10% w/w sodium hydroxide (about 0.2 mL). The mixture was cooled overnight at 5° C. The crystals were collected by filtration, washed with water, and dried under vacuum at 40° C. for two hours to provide N-[4-(4-amino-2-ethyl-1H-imidazo[4,5-c]quinolin-1-yl)butyl]methanesulfonamide as beige crystals, mp 202° C. to 204° C., having a $^1$H NMR spectrum consistent with an authentic sample.

Example 25

Preparation of 5-Amino-2-butyl-1-(1-ethylpropyl)-1H-imidazole-4-carbonitrile

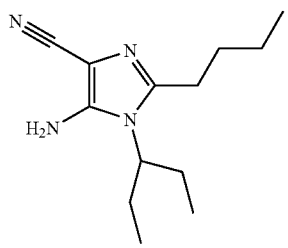

Aminomalononitrile p-toluenesulfonate (1.00 g, 3.95 mmol), pyridine (0.32 mL, 3.95 mmol), and trimethyl orthovalerate (1.36 mL, 7.90 mmol) were combined in acetonitrile (16 mL), and the solution was heated at 85° C. for 1 hour. 3-Aminopentane (0.7 mL, 6 mmol) was added, and the reaction was heated for 1 hour and ten minutes and then allowed to cool to room temperature overnight. The solvent was removed under reduced pressure, and the resulting oil was partitioned between aqueous sodium bicarbonate and ethyl acetate. The ethyl acetate layer was separated and washed with aqueous sodium bicarbonate, water, and brine. The combined aqueous fractions were extracted with ethyl acetate, and the combined organic fractions were dried over sodium sulfate, filtered, and concentrated under reduced pressure to provide 1.04 g of crude 5-amino-2-butyl-1-(1-ethylpropyl)-1H-imidazole-4-carbonitrile as a brown oil. $^1$H-NMR (300 MHz, CDCl$_3$) δ 3.90-3.78 (m, 1H), 3.71 (br s, 2H), 2.55 (m, 2H), 0.95 (t, J=7.3, 3H), 0.86 (t, J=7.4, 6H); MS (ESI) m/z (M+1)$^+$235.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method comprising: combining a compound of the formula:

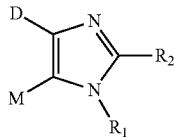

IIIa with a compound of the formula:

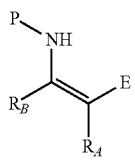

IIa or a salt thereof or
combining a compound of the formula:

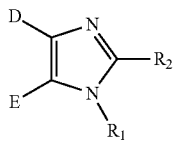

III with a compound of the formula:

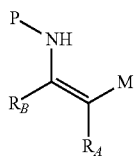

II or a salt thereof to form a compound of the formula:

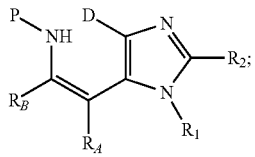

wherein:
D is selected from the group consisting of —C≡N, —C(O)—O—$C_{1-4}$alkyl, —C(O)—NH$_2$, —C(O)—H, —CH$_2$OH, and —CH$_2$OC$_{1-4}$alkyl;
E is selected from the group consisting of —Cl, —Br, —I, —OS(O)$_2$CF$_3$, and —N$_2$$^+$BF$_4$$^-$;
M is selected from the group consisting of —B(OH)$_2$, —B(O-alkyl)$_2$, —Sn(alkyl)$_3$, —Zn-Halide,

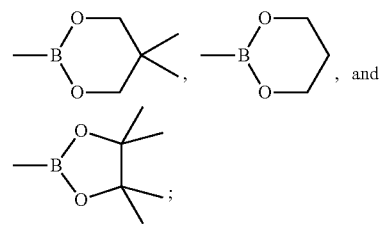

P is selected from the group consisting of hydrogen, —C(O)—$C_{1-4}$alkyl, —C(O)—O—$C_{1-4}$alkyl, benzyl, and p-methoxybenzyl, or —NHP is replaced by a 2,5-dimethylpyrrole;
$R_A$ and $R_B$ taken together form a fused benzene ring or fused pyridine ring wherein the benzene ring or pyridine ring is unsubstituted or substituted by one or more R groups, or substituted by one $R_3$ group, or substituted by one $R_3$ group and one R group; wherein:
R is selected from the group consisting of:
halogen,
hydroxy,
alkyl,
haloalkyl,
alkoxy, and
—N($R_9$)$_2$;
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
$R_3$ is selected from the group consisting of:
—Z—$R_4$,
—Z—X—$R_4$,
—Z—X—Y—$R_4$,
—Z—X—Y—X—Y—$R_4$, and
—Z—X—$R_5$;
X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,

—CH(—N(—O—R$_8$)-Q-R$_4$)—,

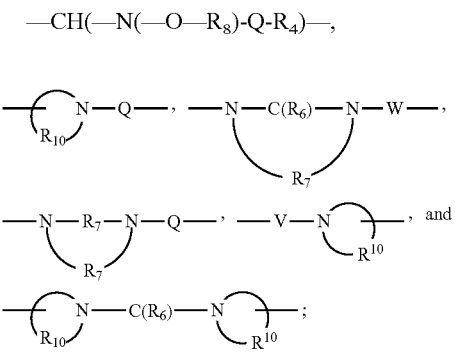

Z is a bond or —O—;
R$_4$ is selected from the group consisting of hydrogen, alkyl, alkenyl, alkynyl, aryl, arylalkylenyl, arloxyalkylenyl, alkylarylenyl, heteroaryl, heteroarylalkylenyl, heteroaryloxyalkylenyl, alkyleheteroarylenyl, and heterocyclyl wherein the alkyl, alkenyl, alkynyl, aryl, arylalylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substitutents independently selected from the group consisting of alkyl, aloxy, hydroxyalkyl, haloalkyl, haloalkoxy, halogen, nitro, hydroxy, mercapto, cyano, aryl, aryloxy, arylalkleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
R$_5$ is selected from the group consisting of:

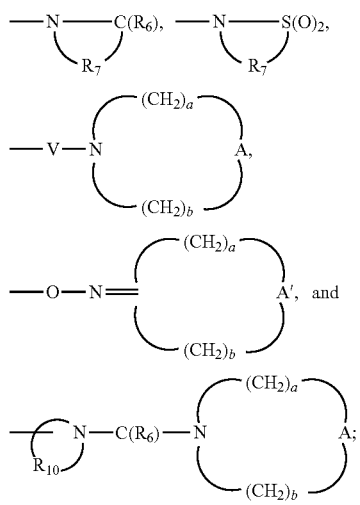

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, and N(R$_4$)—;

M is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7.

2. A method comprising:
providing a compound of the formula:

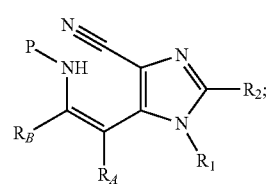

and exposing the compound of Formula IV' to conditions to cause an intramolecular cyclization and formation of a compound of the formula:

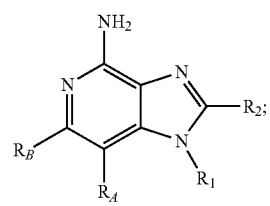

wherein:
P is selected from the group consisting of hydrogen, —C(O)—C$_{1-4}$alkyl, —C(O)—O—C$_{1-4}$alkyl, benzyl, and p-methoxybenzyl, or —NHP is replaced by a 2,5-dimethylpyrrole;
R$_A$ and R$_B$ taken together form a fused benzene ring or fused pyridine ring wherein the benzene ring or pyridine ring is unsubstituted or substituted by one or more R groups, or substituted by one R$_3$ group, or substituted by one R$_3$ group and one R group; wherein:
R is selected from the group consisting of:
  halogen,
  hydroxy,
  alkyl,
  haloalkyl,
  alkoxy, and
  —N(R$_9$)$_2$;
R$_1$ is selected from the group consisting of:
  —R$_4$,
  —X—R$_4$,
  —X—Y—R$_4$,
  —X—Y—X—Y—R$_4$, and
  —X—R$_5$;

R₂ is selected from the group consisting of:
- —R₄,
- —X—R₄,
- —X—Y—R₄, and
- —X—R₅;

R₃ is selected from the group consisting of:
- —Z—R₄,
- —Z—X—R₄,
- —Z—X—Y—R₄,
- —Z—X—Y—X—Y—R₄, and
- —Z—X—R₅;

X is selected from the group consisting of alkylene, alkenylene, alkynylene, arylene heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
- —O—,
- —S(O)₀₋₂—,
- —S(O)₂—N(R₈)—,
- —C(R₆)—,
- —C(R₆)—O—,
- —O—C(R₆)—,
- —O—C(O)—O—,
- —N(R₈)-Q-,
- —C(R₆)—N(R₈)—,
- —O—C(R₆)—N(R₈)—,
- —C(R₆)—N(OR₉)—,
- —O—N(R₈)-Q-,
- —O—N=C(R₄)—,
- —C(=N—O—R₈)—,
- —CH(—N(—O—R₈)-Q-R₄)—,

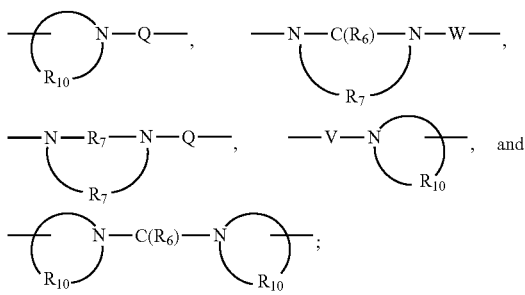

Z is a bond or —O—;

R₄ is selected from the group consisting of hydrogen, alkyl, alkenyl, atkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, hetemaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, meroapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of:

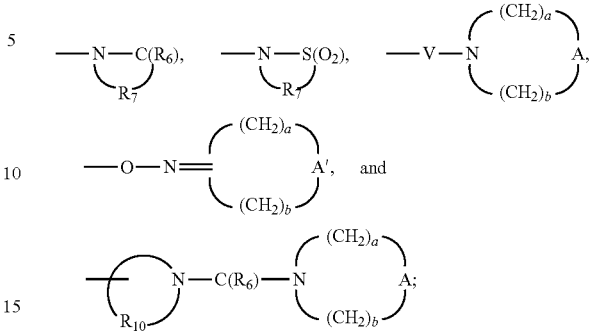

R₆ is selected from the group consisting of =O and =S;
R₇ is C₂₋₇ alkylene;
R₈ is selected from the group consisting of hydrogen, alkyl, alkoxyalkylenyl, hydroxyalkylenyl, arylalkylenyl, and heteroarylalkylenyl;
R₉ is selected from the group consisting of hydrogen and alkyl;
R₁₀ is C₃₋₈ alkylene;
A is selected from the group consisting of —O—, —C(O)—, —S(O)₀₋₂—, and —N(R₄)—;
A' is selected from the group consisting of —O—, —N(-Q-R₄)—, and —CH₂;
Q is selected from the group consisting of a bond, —C(R₆)—, —C(R₆)—C(R₆)—, —S(O)₂—, —C(R₆)—N(R₈)—W—S(O)₂—N(R₈)—, —C(R₆)—O—, —C(R₆)—S—, and —C(R₆)—N(OR₉)—;
V is selected from the group consisting of —C(R₆)—, —O—C(R₆)—, —N(R₈)—C(R₆)—, and —S(O)₂—;
W is selected from the group consisting of a bond, —C(O)—, and —S(O)₂—; and
a and b are independently integers from 1 to 6 with the proviso that a+b is ≦7.

3. The method of claim 2 wherein R₁ is selected from the group consisting of 2-methylpropyl, 2-hydroxy-2-methylpropyl, 2-(propylsulfonyl)ethyl, 2-methyl-2-[(methylsulfonyl)amino]propyl, 4-[(morpholin-4-ylcarbonyl)amino]butyl, and 4-methanesulfonylaminobutyl.

4. The method of claim 2 wherein R₁ is 4-methanesulfonylaminobutyl.

5. The method of claims 2 wherein R₂ is selected from the group consisting of hydrogen, methyl, ethyl, propyl, butyl, 2-methoxyethyl, 2-hydroxyethyl, ethoxymethyl, and hydroxymethyl.

6. The method of claim 2 where R₂ is ethyl.

7. A compound of the formula:

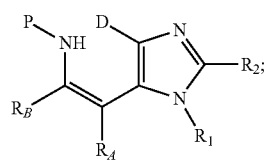

IV wherein:
D is selected from the group consisting of —C≡N, —C(O)—O—C₁₋₄alkyl, —C(O)—NH₂, —C(O)—H, —CH₂OH, and —CH₂OC₁₋₄alkyl;

P is selected from the group consisting of hydrogen, —C(O)—C$_{1-4}$alkyl, —C(O)—O—C$_{1-4}$alkyl benzyl, and p-methoxybenzyl, or —NHP is replaced by a 2,5-dimethylpyrrole;

R$_A$ and R$_B$ taken together form a fused benzene ring or fused pyridine ring wherein the benzene ring or pyridine ring is unsubstituted or substituted by one or more R groups, or substituted by one R$_3$ group, or substituted by one R$_3$ group and one R group; wherein:

R is selected from the group consisting of:
halogen,
hydroxy,
alkyl,
haloalkyl,
alkoxy, and
—N(R$_9$)$_2$;

R$_1$ is selected from the group consisting of:
—R$_4$,
—X—R$_4$,
—X—Y—R$_4$,
—X—Y—X—Y—R$_4$, and
—X—R$_5$;

R$_2$ is selected from the group consisting of:
—R$_4$,
—X—R$_4$,
—X—Y—R$_4$, and
—X—R$_5$;

R$_3$ is selected from the group consisting of:
—Z—R$_4$,
—Z—X—R$_4$,
—Z—X—Y—R$_4$,
—Z—X—Y—X—Y—R$_4$, and
—Z—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

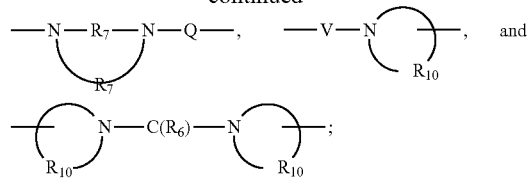

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyan, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

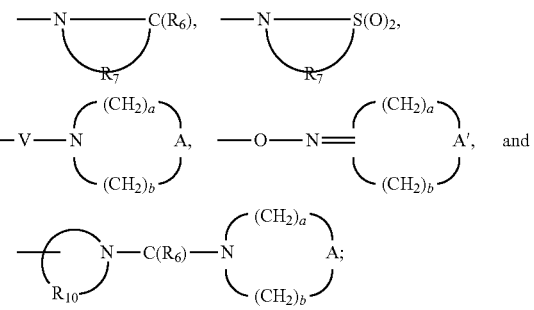

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, and N(R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$);
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;

or a pharmaceutically acceptable salt thereof.

8. The compound of claim 7 wherein $R_1$ is selected from the group consisting of 2-methylpropyl, 2-hydroxy-2-methylpropyl, 2-(propylsulfonyl)ethyl, 2-methyl-2-[(methylsulfonyl)amino]propyl, 4-[(morpholin-4-ylcarbonyl)amino]butyl, and 4-methanesulfonylaminobutyl.

9. The compound of claim 7 wherein $R_1$ is 4-methanesulfonylaminobutyl.

10. The compound of claim 7 wherein $R_2$ is selected from the group consisting of hydrogen, methyl, ethyl, propyl, butyl, 2-methoxyethyl, 2-hydroxyethyl, ethoxymethyl, and hydroxymethyl.

11. The compound of claim 7 wherein $R_2$ is ethyl.

12. The method of claim 4 wherein $R_2$ is ethyl.

13. The compound of claim 9 wherein $R_2$ is ethyl.

14. The compound of claim 7 wherein D is —C≡N.

15. The compound of claim 7 wherein P is hydrogen.

16. The compound of claim 7 wherein $R_A$ and $R_B$ taken together form a fused benzene ring or fused pyridine ring wherein the benzene ring or pyridine ring is unsubstituted.

17. The compound of claim 16 wherein $R_A$ and $R_B$ taken together form a fused benzene ring that is unsubstituted.

18. The compound of claim 8 wherein $R_1$ is selected from the group consisting of 2-hydroxy-2-methylpropyl, 2-(propylsulfonyl)ethyl, 2-methyl-2-[(methylsulfonyl)amino]propyl, 4-[(morpholin-4-ylcarbonyl)amino]butyl, and 4-methanesulfonylaminobutyl.

19. The compound of claim 8 wherein $R_1$ is 2-methylpropyl.

20. The compound of claim 10 wherein $R_2$ is selected from the group consisting of methyl, ethyl, propyl, butyl, 2-methoxyethyl, 2-hydroxyethyl, ethoxymethyl, and hydroxymethyl.

21. The compound of claim 10 wherein $R_2$ is hydrogen.

\* \* \* \* \*